(12) United States Patent
Neuzil et al.

(10) Patent No.: US 9,896,466 B2
(45) Date of Patent: Feb. 20, 2018

(54) TAMOXIFEN DERIVATIVES FOR TREATMENT OF NEOPLASTIC DISEASES, ESPECIALLY WITH HIGH HER2 PROTEIN LEVEL

(71) Applicants: Smart Brain S.R.O., Prague (CZ); Biotechnologicky Ustav Av Cr, V.V.I., Prague (CZ); Jiri Neuzil, Prague (CZ); KKCG AG, Lucerne (CH)

(72) Inventors: Jiri Neuzil, Prague (CZ); Jan Stursa, Prague (CZ); Lukas Werner, Kadan (CZ)

(73) Assignees: KKCG AG, Lucerne (CH); Biotechnologicky Ustav Av Cr. V.V.I., Prague (CZ); Smart Brain S.R.O., Prague (CZ)

( * ) Notice: Subject to any disclaimer, the term of this patent is extended or adjusted under 35 U.S.C. 154(b) by 0 days.

(21) Appl. No.: 14/786,710

(22) PCT Filed: Apr. 7, 2014

(86) PCT No.: PCT/CZ2014/000035
§ 371 (c)(1),
(2) Date: Oct. 23, 2015

(87) PCT Pub. No.: WO2014/173374
PCT Pub. Date: Oct. 30, 2014

(65) Prior Publication Data
US 2016/0075726 A1    Mar. 17, 2016

(30) Foreign Application Priority Data

Apr. 24, 2013  (CZ) .................................... 2013-308
Jan. 29, 2014  (CZ) .................................... 2014-66

(51) Int. Cl.
*C07F 9/54*    (2006.01)
*A61K 31/135*  (2006.01)

(52) U.S. Cl.
CPC .......... *C07F 9/5456* (2013.01); *C07F 9/5442* (2013.01); *C07F 9/5449* (2013.01)

(58) Field of Classification Search
CPC ..... C07F 9/5456; C07F 9/5442; C07F 9/5449
See application file for complete search history.

(56) References Cited

PUBLICATIONS

Smith, R.A.J., "Delivery of bioactive molecules to mitochondria in vivo." Proceedings of the National Academy of Sciences 100.9 (2003): 5407-5412.*
Biasutto, L., "Mitochondrially targeted anti-cancer agents." Mitochondrion 10.6 (2010): 670-681.*
Neuzil, J., "Molecular mechanism of 'mitocan'-induced apoptosis in cancer cells epitomizes the multiple roles of reactive oxygen species and Bcl-2 family proteins." FEBS letters 580.22 (2006): 5125-5129.*
Parvez, S., "Taurine Prevents Tamoxifen-Induced Mitochondrial Oxidative Damage in Mice." Basic & clinical pharmacology & toxicology 102.4 (2008): 382-387.*
Saal, C.,"Pharmaceutical salts: a summary on doses of salt formers from the Orange Book." European Journal of Pharmaceutical Sciences 49.4 (2013): 614-623.*
Moreira, P.I., "Tamoxifen and estradiol interact with the flavin mononucleotide site of complex I leading to mitochondrial failure." Journal of Biological Chemistry 281.15 (2006): 10143-10152.*
C. DeSantis et al., "Breast Cancer Statistics, 2011", CA Cancer J. Clin., vol. 61, No. 6, pp. 409-418 (2011).
Y. Ding et al., "Receptor Tyrosine Kinase ErbB2 Translocates into Mitochondria and Regulates Cellular Metabolism", Nature Communications, vol. 3, pp. 1-12 (2012).
L-F Dong et al., "Alpha-Tocopheryl Succinate Induces Apoptosis by Targeting Ubiquinone-Binding Sites in Mitochondrial Respiratory Complex II", Oncogene, vol. 27, pp. 4324-4335 (2008).
L-F Dong et al., "Mitochondrial Targeting of Alpha-Tocopheryl Succinate Enhances its Pro-Apoptotic Efficacy: A New Paradigm for Effective Cancer Therapy", Free Radical Biol. & Med., vol. 50, pp. 1546-1555 (2011).
L-F. Dong et al., "Suppression of Tumor Growth In Vivo by the Mitocan Alpha-Tocopheryl Succinate Requires Respiratory Complex II", Clin. Cancer Res., vol. 15, No. 5, pp. 1593-1642 (2009).
L-F. Dong et al., "Mitochondrial Targeting of Vitamin E Succinate Enhances its Pro-Apoptotic and Anti-Cancer Activity via Mitochondrial Complex II", J. Biol. Chem., vol. 286, No. 5, pp. 3717-3728 (2011).
M. S. Ewer et al., "Cardiotoxicity of Anticancer Treatments: What the Cardiologist Needs to Know," Nature Reviews, vol. 7, pp. 564-575 (2010).

(Continued)

*Primary Examiner* — Matt Mauro
(74) *Attorney, Agent, or Firm* — Fitzpatrick, Cella, Harper & Scinto

(57) ABSTRACT

The subject of the invention are new mitochondrially targeted E/Z isomers of aliphatic triphenylphosphonium derivatives of tamoxifen where the aliphatic chain is alkyl or alkenyl, and their corresponding tertiary amine salts and/or their mixture (MitoTAX). Alkyl triphenylphosphonium derivatives of tamoxifen have the general formula (I), where n=8 to 12 and where Z is selected from the group of organic salts or inorganic salts. Alkenyl triphenylphosphonium derivatives of tamoxifen have the general formula IA, where n=6 to 10 and where Z has the above mentioned meaning. These compounds are applicable for the treatment of neoplastic disease, especially those with high HER2 protein levels. The drug for the treatment of neoplastic diseases according to the invention contains at least one E/Z isomer of aliphatic triphenylphosphonium derivatives of tamoxifen of the general formula (I) and/or IA or their corresponding salts of tertiary amine.

13 Claims, 12 Drawing Sheets

(56) References Cited

PUBLICATIONS

Figure 1:
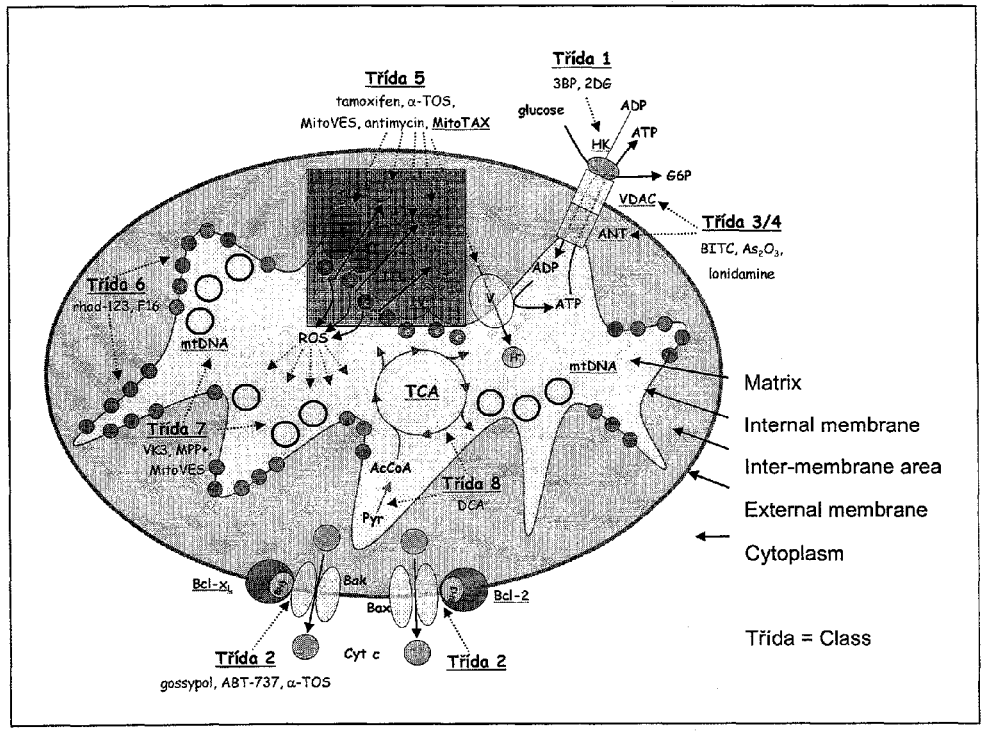

E. R. Ahn et al., "Is the Improved Efficacy of Trastuzumab and Lapatinib Combination Worth the Added Toxicity? A Discussion of Current Evidence, Recommendations, and Ethical Issues Regarding Dual HER2-Targeted Therapy," Breast Cancer: Basic and Clinical Reserach, vol. 6, pp. 191-207 (2012).

M. Gerlinger et al., "Intratumor Heterogeneity and Branched Evolution Revealed by Multiregion Sequencing," N. Engl. J. Med., vol. 366, No. 10, pp. 883-892 (2012).

C. T. Guy et al., "Expression of the Neu Protooncogene in the Mammary Epithelium of Transgenic Mice Induces Metastatic Disease," Proc. Natl. Acad. Sci., vol. 89, pp. 10578-10582 (1992).

D. Hanahan et al., "Hallmarks of Cancer: the Next Generation", Cell, vol. 144, pp. 646-674 (2011).

D. Hanahan et al., "The Hallmarks of Cancer", Cell, vol. 100, pp. 57-70 (2000).

H-Y. Yang et al., "p27 Kip1 Inhibits HER2/new-mediated Cell Growth and tumorigenesis", Oncogene, vol. 20, pp. 3695-3702 (2001).

S. Jones et al., Core Signaling Pathways in Human Pancreatic Cancers Revealed by Global Genomic Analyses, Science, vol. 321, pp. 1801-1806 (2008).

K. Kluckova et al., "Mitochondrial complex II, a Novel Target for Anti-Cancer Agents", Biochimica et Biophysica Acta, vol. 1827, pp. 552-564 (2013).

C. Thomas et al., "The Different Roles of ER Subtypes in Cancer Biology and Therapy", Nature Reviews, vol. 11, pp. 597-608 (2011).

J. Neuzil et al., "Classification of Mitocans, Anti-Cancer Drugs Acting on Mitochondria", Mitochondrion, vol. 13, pp. 199-208 (2013).

D. W. Parsons et al., "An Integrated Genomic Analysis of Human Glioblastoma Multiforme", Science, vol. 321, pp. 1807-1812 (2008).

J. Rohlena et al., "Mitochondrially Targeted Alpha-Tocopheryl Succinate Is Antiangiogenic: Potential Benefit Against Tumor Angiogenesis but Caution Against Wound Healing", Antioxidants & Redox Signaling, vol. 15, No. 12, pp. 2923-2935 (2011).

J. Stingl et al., "Molecular Heterogeneity of Breast Carcinomas and the Cancer Stem Cell Hypothesis", Nature Reviews, vol. 7, pp. 791-799 (2007).

P. E. Tessier et al., "(Z)-Tamoxifen and Tetrasubstituted Alkenes and Dienes via a Regio- and Stereospecific Three-Component Magnesium Carbometalation Palladium(0) Cross-Coupling Strategy", Org. Lett., vol. 5, No. 17, pp. 2989-2992 (2003).

C. L. Arteaga et al., "Treatment of HER2-Positive Breast Cancer: Current Status and Future Perspectives", Nature Reviews, vol. 9, pp. 16-32 (2012).

S-X Lin et al., "Molecular Therapy of Breast Cancer: Progress and Future Directions", Nature Reviews, vol. 6, pp. 485-493 (2010).

D. Wetterskog et al., "Identification of Novel Determinants of Resistance to Lapatinib in ERBB2-Amplified Cancers", Oncogene, vol. 33, pp. 966-976 (2014).

G. Deblois et al., Oestrogen-Related Receptors in Breast Cancer: Control of Cellular Metabolism and Beyond, Nature Reviews, vol. 13, pp. 27-36 (2013).

\* cited by examiner

I.

IA

TAMOXIFEN DERIVATIVES FOR TREATMENT OF NEOPLASTIC DISEASES, ESPECIALLY WITH HIGH HER2 PROTEIN LEVEL

FIELD OF THE INVENTION

The invention concerns new mitochondrially targeted tamoxifen derivatives for treatment of neoplastic diseases, especially tumours with high HER2 (human epidermal growth factor receptor 2) protein level, which influences spontaneous division of cells and growth of tumours.

BACKGROUND OF THE INVENTION

The recent progress in molecular medicine has led to certain improvements in diagnostics and treatment of neoplastic diseases. In spite of this partial success, these pathologies remain a considerable challenge. For certain types of cancers, the current therapy in some cases fails for a number of reasons. On the one hand, it is inherent resistance of tumour cells, their ability of constant mutation and therapy evasion, on the other hand it is also the heterogeneity of the tumour environment (Hanahan D, Weinberg R A. Hallmarks of cancer: the next generation. Cell 2011; 144:646-674). It was shown that tumours of the same type highly differ for individual subjects from the viewpoint of their genomic profile (Jones S et al. Core signalling pathways in human pancreatic cancers revealed by global genomic analyses. Science 2008; 321:1801-1806. Parsons D W et al. An integrated genomic analysis of human glioblastoma multiforme. Science 2008; 321.1807-1812.), which indicates the necessity of the so-called "personal" therapy. Even a bigger problem is the heterogeneity of mutations in the same tumour, as it has been recently shown for renal tumours (Gerlinger M et al. Intratumor heterogeneity and branched evolution revealed by multiregion sequencing. N Engl J Med 2012; 366:883-892.), and this situation can be expected for other types of tumours as well. For this reason it is necessary to search for new approaches and for an invariable intervention point(s) common for all or most malignant cells in the tumour and which preferably affects essential functions in cancer cells. It seems that such an intervention point could be mitochondria, i.e. organelles which are fundamental for the generation of energy necessary for all physiological as well as pathophysiological processes in cells. Although tumour cells use, from a major part, the so-called aerobic glycolysis for energy generation, mitochondrial respiration (i.e. consumption of oxygen linked to ATP formation) is inherent to most (if not all) types of tumours (Ralph S J et al. The causes of cancer revisited: "mitochondrial malignancy" and ROS-induced oncogenic transformation—why mitochondria are targets for cancer therapy. Mol Aspects Med 2010; 31:145-170.).

A group of substances with anti-cancer activity was defined under the name "mitocans" (derived from "mitochondria and cancer") (Neuzil J et al. Molecular mechanism of 'mitocan'-induced apoptosis in cancer cells epitomizes the multiple roles of reactive oxygen species and Bcl-2 family proteins. FEBS Lett 2008; 580:5125-5129. Neuzil J et al. Classification of mitocans, anti-cancer drugs acting on mitochondria. Mitochondrion 2013; 13:199-208.). These substances are divided into several groups according to the molecular mechanism of their activity. These are: (1) hexokinase inhibitors; (2) agents targeting Bcl-2 family proteins; (3) redox-active agents acting as thiol inhibitors; (4) agents targeting the VDAC and ANT proteins; (5) agents targeted the electron redox chain; (6) lipophilic targeting the internal mitochondrial membrane; (7) agents targeting the Krebs cycle; (8) agents targeting the mitochondrial DNA; (9) agents that belong to none of these groups. Examples of these agents and their targets are shown in FIG. 1.

Breast cancer is a neoplastic disease which is very difficult to treat and which is currently diagnosed at one in eight women during their life-span. Treatment of breast cancer commonly based on tamoxifen (TAX) therapy. Approximately 30% of breast cancer patients are diagnosed with high level of the HER2 protein, which belongs to the group of receptor tyrosine kinases and which increases the proliferative capacity of cells, enhancing their malignant potential (Arteaga C L et al. Treatment of HER2-positive breast cancer: current status and future perspectives. Nat Rev Clin Oncol. 2011; 9:16-32.). The established therapy (where the main drug used is TAX) is ineffective because tumours featuring high HER2 levels are rather resistant to this therapy. TAX affects oestrogen receptors in the plasma membrane of breast cancer cells, whereby it inhibits important processes linked to the for proliferation capacity of cancer cells. It has been published recently that at higher concentrations, TAX acts not only via the oestrogen receptor, but it also moves to the inner mitochondrial membrane, where it interacts with complex I of the respiratory chain (Moreira P I et al. Tamoxifen and estradiol interact with the flavin mononucleotide site of complex I leading to mitochondrial failure. J Biol Chem 2006; 281:10143-10152.). This occurs, however, at doses which are not easy to achieve from a pharmacological point of view. Moreover, it is possible to expect an increased toxicity of TAX in case of such high doses.

At present, breast cancer with high HER2 protein is treated with the humanised antibody "trastuzumab", which inhibits HER2 activity. This therapy is economically highly demanding and features a secondary toxicity; furthermore a large percentage of subjects with high HER2 protein are resistant to trastuzumab (it is estimated to be about 30%). Rather challenging is also the recently introduced drug lapatinib that inhibits receptor tyrosine kinases (Ewer M S, Ewer S M. Cardiotoxicity of anticancer treatments: what the cardiologist needs to know. Nat Rev Cardiol 2010; 7:564575. Lin S X et al. Molecular therapy of breast cancer: progress and future directions. Nat Rev Endocrinol 2010; 6:485-493. Ahn E R et al. is the improved efficacy of trastuzumab and lapatinib combination worth the added toxicity? Breast Cancer 2012; 6:191-207.). An issue in this context is that lapatinib is not a specific HER2 inhibitor, which may lead to the inhibition of other receptor tyrosine kinases, too, and to secondary toxicity, and it is also possible to anticipate development of resistance to this therapy (Wetterskog D et al. Identification of novel determinants of resistance to lapatinib in ERBB2-amplified cancers. Oncogene 2013; 1-11).

SUMMARY OF THE INVENTION

For the above mentioned reasons, we designed and synthesized a group of agents efficient against tumours with high levels of the HER2 protein, which directly target mitochondria and which may overcome the above mentioned complications. These disadvantages associated with tamoxifen (TAX) are eliminated by tagging it with a triphenylphosphonium via an aliphatic chain (referred to as MitoTAX), where the chain is alkyl or alkenyl, and their corresponding tertiary amine salts, selected from the group of organic salts, such as citrate, acetate, lactate, tartarate, oxalate, ascorbate, mesylate, tosylate or inorganic salts, such as sulphate, halogenide, phosphate and/or their mixtures, alkyl triphenylphosphonium derivatives of tamoxifen have the general formula I,

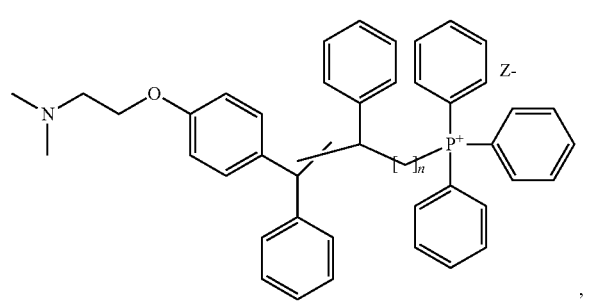

I where n=8 to 12, and where Z is selected from the group of organic salts, such as citrate, acetate, lactate, tartarate, oxalate, ascorbate, mesylate, tosylate or inorganic salts, such as e.g. sulphate, halogenide, phosphate, and wherein the crossed double bond in the general formula I, situated in the TAX moiety, indicates that the double bond may have E and/or Z configuration, and alkenyl triphenylphosphonium derivatives of tamoxifen have the general formula IA

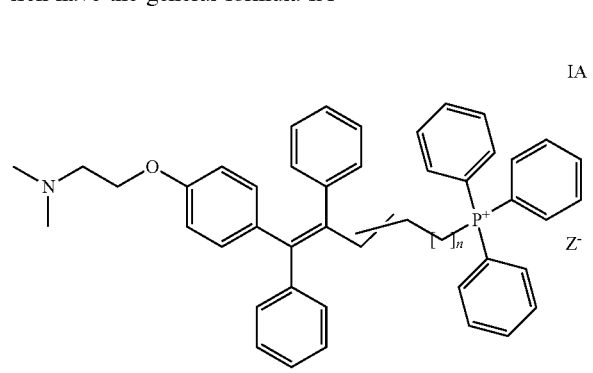

IA where n=6 to 10, and where Z has the meaning stated above, and wherein the crossed double bond in the general formula IA, situated in the side chain indicates that the double bond may have E and/or Z configuration.

The method of preparation of alkyl triphenylphosphonium derivatives of tamoxifen of the general formula I is based on a reaction of ylide generated from tert-butyldimethylsilyl-oxy-alkyl-triphenylphosphonium with the general formula II,

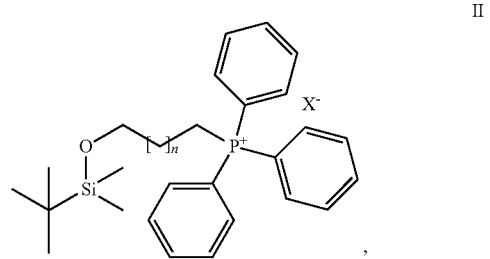

II where n=5 to 9
and X is I, Br, Cl or mesyl,
under the treatment of organic base (preferably butyl lithium) in tetrahydrofuran (THF) under an argon atmosphere at the temperature of −78° C. and subsequent condensation with aldehyde, of the formula III,

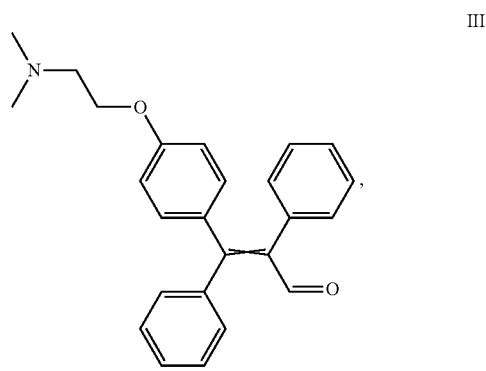 [SMILES: CN(C)CCOc1ccc(C(=C(C=O)c2ccccc2)c2ccccc2)cc1]

III affording a silylated derivative of the general formula IV,

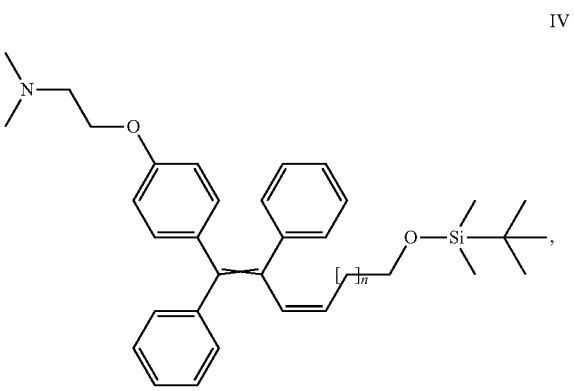

IV where n=5 to 9.

The silylated derivative of the general formula IV is treated with tetrabutylammonium fluoride affording alkenol of the general formula V,

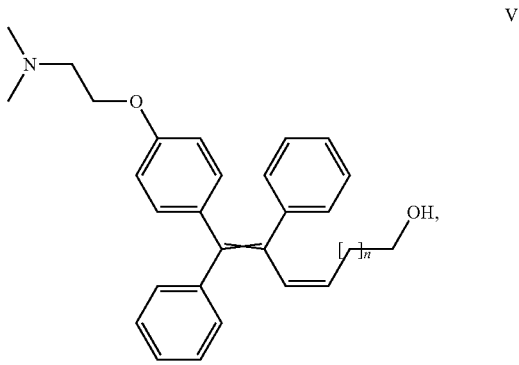

V where n=5 to 9,
which is reduced in the hydrogen atmosphere at the presence of a catalyst to alcohol of the general formula VI,

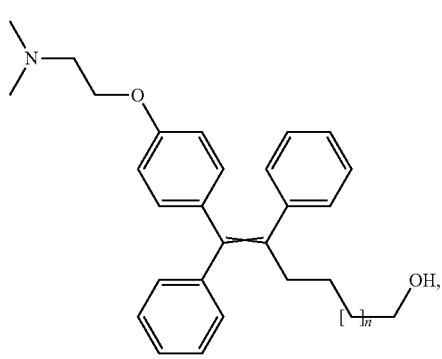

where n=5 to 9, the alcohol of the general formula VI is substituted to the corresponding derivative of the general formula VII,

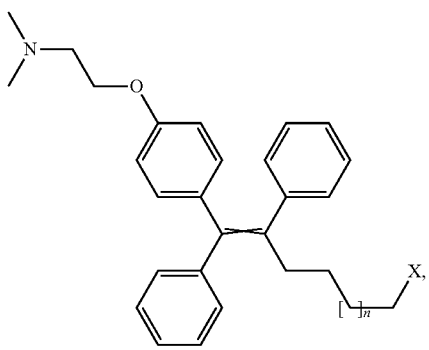

where n=5 to 9
and X is I, Br, Cl or mesyl, which is converted to the mitochondrially targeted alkyl-triphenylphosphonium derivative of tamoxifen of the general formula I by heating together with triphenylphosphine.

Alkenol of the general formula V can be prepared also directly from aldehyde III by reaction with a corresponding (hydroxyalkyl)triphenylphosphonium bromide under the treatment of base (advantageously lithium hexamethyldisilazane) at room temperature and in the mixture of THF and dimethyl sulphoxide (DMSO), which increases solubility of (hydroxyalkyl)triphenylphosphonium bromide. It quickens and cheapens the synthesis considerably.

When alkenol of the general formula V is used in the form of a tertiary nitrogen salt, it is possible to increase the yield of the alcohol of the general formula VI acquired by the procedure mentioned above, affording the corresponding tertiary amine salt of the triphenylphosphonium derivative of tamoxifen of the general formula I without isolating the compound of the general formula VII.

The method of preparation of alkenyl triphenylphosphonium derivatives of tamoxifen of the general formula IA is based on preparation of ylide generated from alkyl bis(triphenylphosphonium) of the general formula VIII

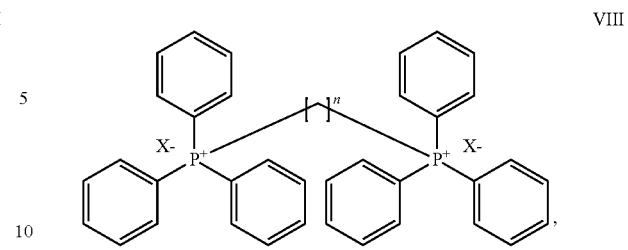

where n=7 to 11
and X is I, Br, Cl or mesyl or a combination thereof, in the mixture of tetrahydrofuran (THF) and dimethyl sulphoxide (DMSO) in argon atmosphere at room temperature under the treatment of organic base (advantageously lithium hexamethyldisilazane) and its subsequent condensation with aldehyde of the formula III.

Alkyl bis(triphenylphosphonium) of the general formula VIII is prepared by a reaction of the corresponding alkyl with triphenylphosphine at an increased temperature.

The cationic triphenylphosphonium (TPP$^+$) group enables interaction of the alkyl or alkenyl triphenylphosphonium derivative of TAX—the agent of the general formula I or IA—with mitochondria. These compounds were prepared by the addition of the cationic group of alkyl-TPP$^+$ to the TAX molecule. In the biological environment, the positive charge on phosphorus of the TPP$^+$ group is delocalised, which means that the substance behaves neutrally. The only exception are cellular structures with negative potential, which is the internal surface of the plasma membrane and, in particular, the inner mitochondrial membrane.

In this environment, the charge is localized on phosphorous and the positively charged TPP+ group acts as an anchor, causing considerable concentration of alkyl or alkenyl TPP+ derivatives of TAX of the general formula I or IA (MitoTAX) at interphase of the mitochondrial matrix and the inner mitochondria membrane.

The MitoTAX molecule is oriented in such a way, that the part with the TPP+ group is positioned within the mitochondrial matrix, and the biologically active part is in the inner mitochondrial membrane, which is the location of the molecular target of MitoTAX, which is the mitochondrial complex I.

For the physical interaction of the biologically active part of MitoTAX with the mitochondrial complex I, a component of the inner mitochondrial membrane, it is necessary that an aliphatic chain of a certain length should be situated between the biologically active part of MitoTAX and the TPP+ group, and it seems that it is not essential whether the aliphatic chain is alkyl or alkenyl—see example 24. From the viewpoint of biological and physico-chemical properties of the mitochondrial membrane, it seems that an ideal length of the aliphatic chain is 8 to 12 carbons.

MitoTAX is markedly more efficient in killing breast cancer cells than the original TAX. Another very important finding is that MitoTAX kills breast cancer cells more efficiently in case of cells with high expression of the HER2 protein than cells with low expression of the HER2 protein. However, it is opposite for TAX, and for this reason TAX is clinically inefficient against breast cancer with high HER2. The reason for increased sensitivity of breast cancer cells with a high HER2 protein level to MitoTAX is likely due to the location of the HER2 protein also in mitochondria, and for cells with low or very low expression of HER2 this oncoprotein is localised in the plasmatic membrane of tumour cells.

The substance known as trastuzumab (Herceptin), which is used as a therapy for breast cancer with high HER2 protein is inefficient in a number of cases. A possible reason is that in the case of high HER2 protein, its significant portion is localised in mitochondria and during trastuzumab effects on tumour cells the transfer of the HER2 protein into mitochondria is further intensified. Cancer cells thus 'hide' HER2 from trastuzumab, which is an inhibitor of its activity. The mitochondrial association of HER2 also changes the mitochondrial metabolism in such a way that the cancer cell moves towards glycolysis and survives better in an environment which is poor in nutrients and oxygen.

Unlike trastuzumab, MitoTAX enters the cell and accumulates in mitochondria on the basis of the negative potential on the internal surface of the inner mitochondrial membrane. Breast cancer cells with high HER2 protein, in many cases resistant to trastuzumab, are more sensitive to Mito-TAX.

An important property of MitoTAX is its efficient inhibition of growth of spontaneous breast cancer with high HER2 protein in a mouse model when the growth is inhibited by 90%, and TAX efficacy is approximately 20 to 30 times lower. Further, MitoTAX is non-toxic to mice.

Breast cancers are heterogeneous from the viewpoint of HER2 protein expression. It is possible to expect that only a part of the tumour will respond to trastuzumab therapy, while MitoTAX will be efficient, since it kills cells with both low and high HER2 protein expression.

Vitamin E succinate was described as a mitocan affecting the mitochondrial complex II (Dong L F et al. α-Tocopheryl succinate induces apoptosis by targeting ubiquinone-binding sites in mitochondrial respiratory complex II. Oncogene 2008; 27:4324-4335. Dong L F et al. Suppression of tumour growth in vivo by the mitocan α-tocopheryl succinate requires respiratory complex II. Clin Cancer Res 2009; 15:1593-1600.). Quite recently we have prepared and tested a substance which arose through addition of the TPP+ group to vitamin E succinate. This new substance is targeted at the same molecular site, its activity is, however, higher than the activity of the parental vitamin E succinate, due to the increased concentration of this substance at the interphase of the inner mitochondrial membrane and mitochondrial matrix. (Dong L F et al. Mitochondrial targeting of vitamin E succinate enhances its pro-apoptotic and anti-cancer activity via mitochondrial complex II. J Biol Chem 2011; 286: 3717-3728. Dong L F et al. Mitochondrial targeting of α-tocopheryl succinate enhances its pro-apoptotic efficacy: A new paradigm of efficient anti-cancer therapy. Free Radic Biol Med 2011; 50:1546-1555. Rohlena J et al Mitochondrially targeted α-tocopheryl succinate is antiangiogenic: Potential benefit against tumour angiogenesis but caution against wound healing. Antiox Redox Signal 2011; 15:2923-2935.). In a similar way as vitamin E succinate with addition of the TPP+ group, MitoTAX accumulates largely at the interphase of the inner mitochondrial membrane and mitochondrial matrix. Nevertheless, MitoTAX affects, according to the invention, the mitochondrial complex I, whereby a change arises in its spectrum of effects compared to TAX, which affects prevailingly oestrogen receptors in the plasma membrane of breast cancer cells, and thus it inhibits their activity important for proliferative properties of cancer cells.

MitoTAX accumulates in mitochondria, it triggers cellular death selectively in cancer cells, whose mitochondria feature higher negative potential in comparison to mitochondria of normal cells. It kills, in a very efficient way, breast cancer cells with high HER2 and is efficient against breast cancer with high HER2, where the target site for MitoTAX is the mitochondrial complex I (see FIG. 1).

MitoTAX can be used for the preparation of drugs for the treatment of neoplastic diseases, especially carcinomas, sarcomas, lymphomas and leukaemias, i.e. for diseases selected from the group:

astrocytoma, neuroblastoma, glioblastoma, mesothelioma, prostate cancer, non-small cell lung cancer, cervical cancer, osteosarcoma, colorectal cancer, hepatocellular carcinoma, leukaemia.

LIST OF ABBREVIATIONS

DCM dichloromethane
DMSO dimethyl sulphoxide
ERα oestrogen receptor-α
ESI MS Electrospray ionization mass spectrometry
HER2 human epidermal growth factor receptor 2
IBX 2-iodoxybenzoic acid
LiHMDS lithium hexamethyldisilazan
MitoTAX mitochondrially targeted tamoxifen
MitoVES mitochondrially targeted vitamin E succinate
NMR nuclear magnetic resonance
TAX tamoxifen
TBAF tetrabutylammonium fluoride
THF tetrahydrofuran
TLC thin layer chromatography

OVERVIEW OF FIGURES

FIG. 1: illustrates classification of individual classes of mitocans, potentially anti-cancer substances acting on mitochondria.

Figure 2:
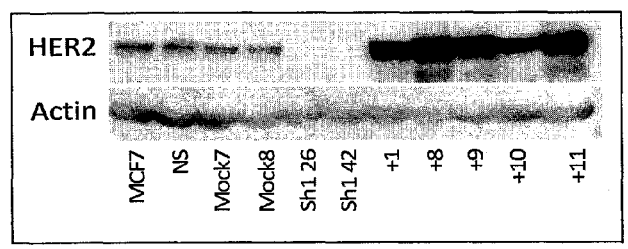

FIG. 2: illustrates preparation of sublines of human breast cancer MCF7.

Figure 3:
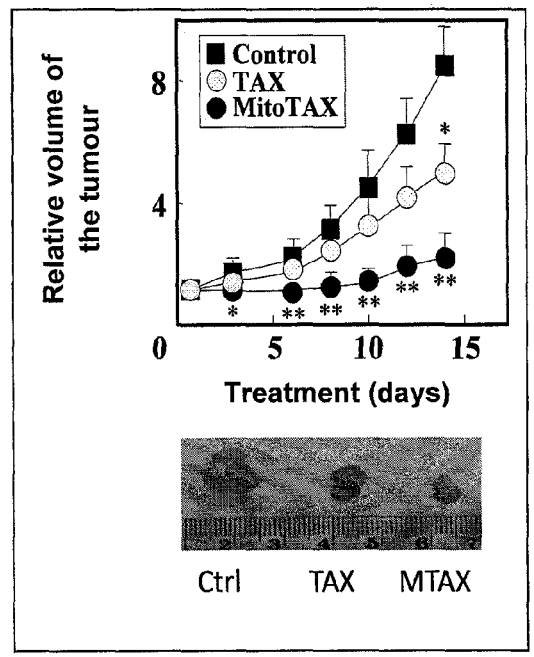

FIG. 3: illustrates the effects of MitoTAX and TAX on the growth of experimental tumours with high HER2 expression.

Figure 4:
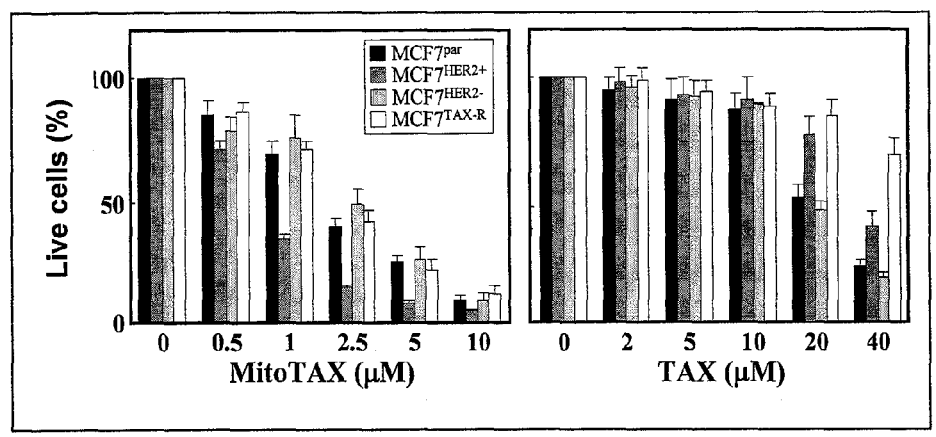

FIG. 4: illustrates apoptosis induced by MitoTAX and TAX in different cell lines.

Figure 5:
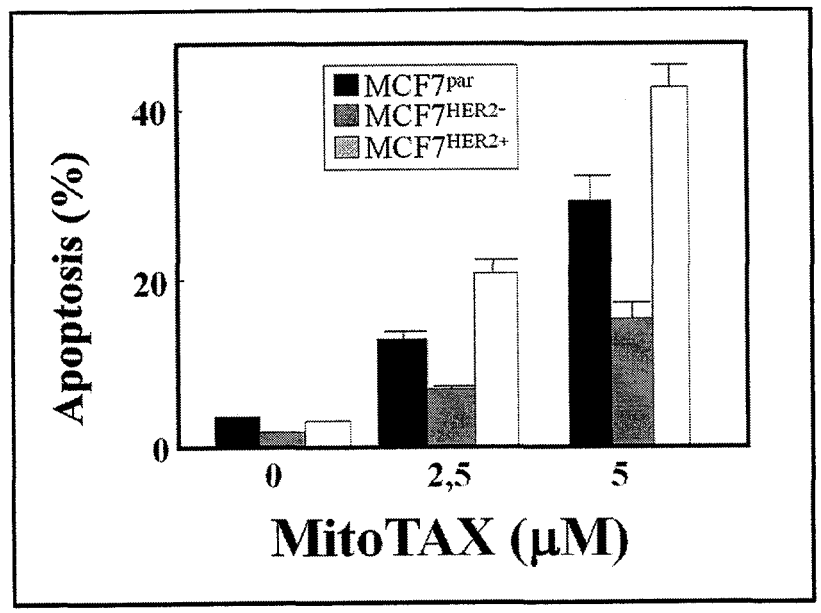

FIG. 5: illustrates the concentration-dependent induction of apoptosis by MitoTAX in various breast cancer cell lines with high HER2 level.

Figure 6:
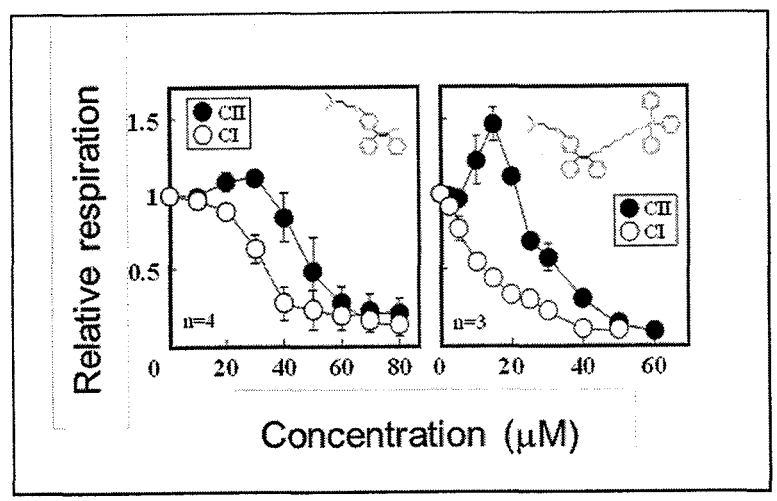

FIG. 6: illustrates how MitoTAX at different concentrations affects the respiration via the mitochondrial complex I and II in tumour cells.

Figure 7:
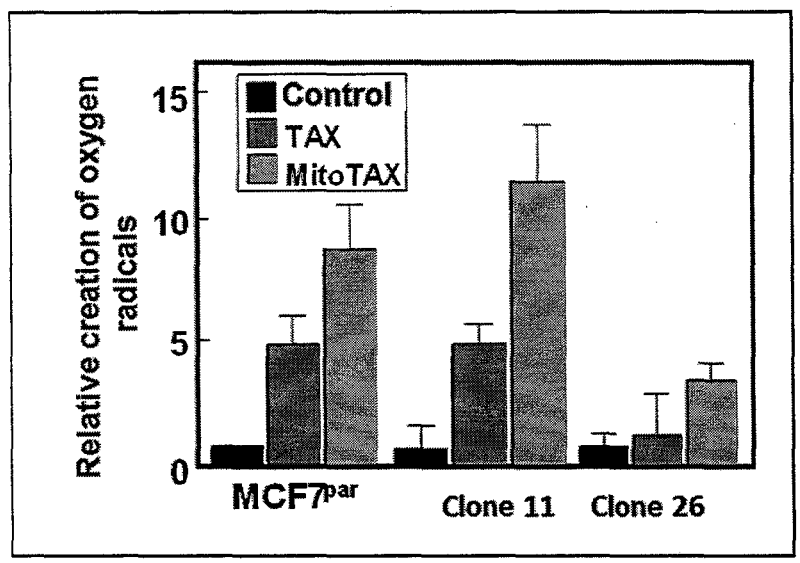

FIG. 7: shows the comparison of the formation of oxygen radicals in breast cancer cells exposed to MitoTAX and TAX.

Figure 8:
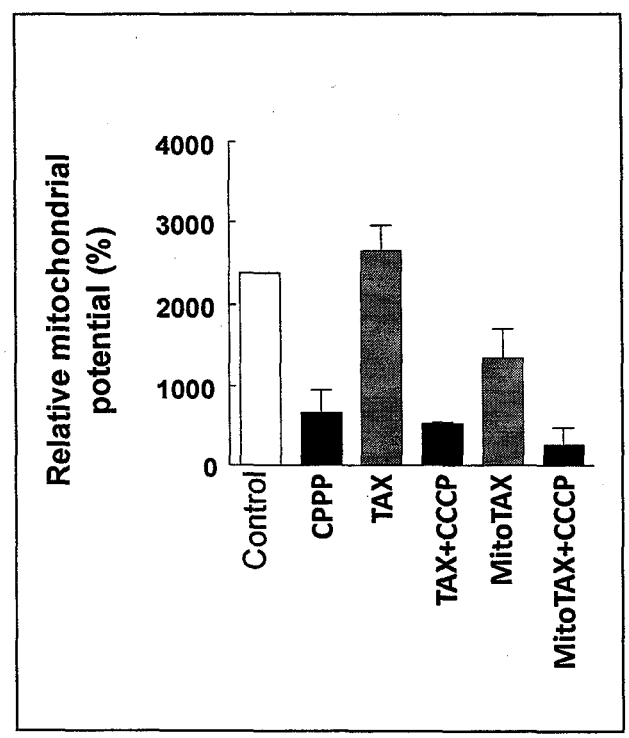

FIG. 8: illustrates to decrease in mitochondrial potential in response to MitoTAX and TAX.

Figure 9:
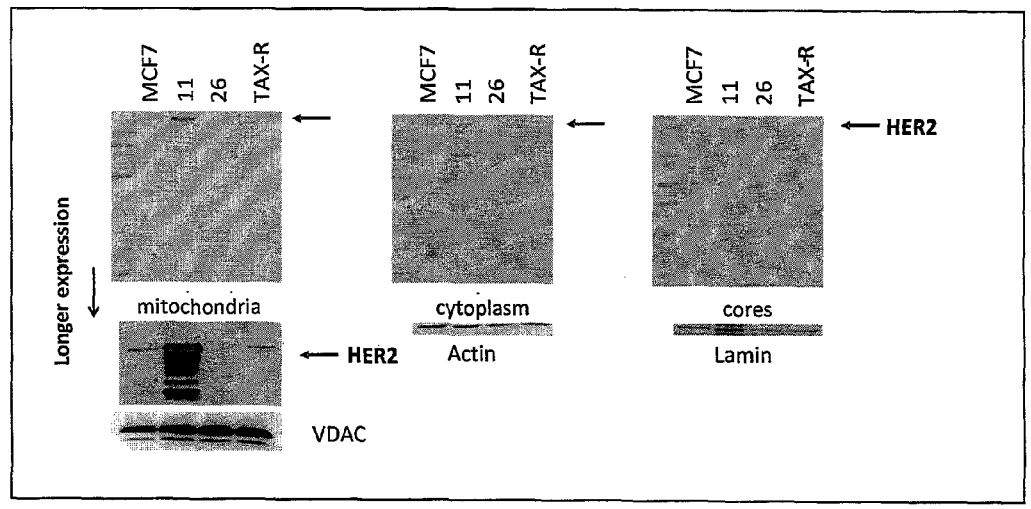

FIG. 9: shows that HER2 is localised preferentially in mitochondria of breast cancer cells with high expression of HER2.

Figure 10:
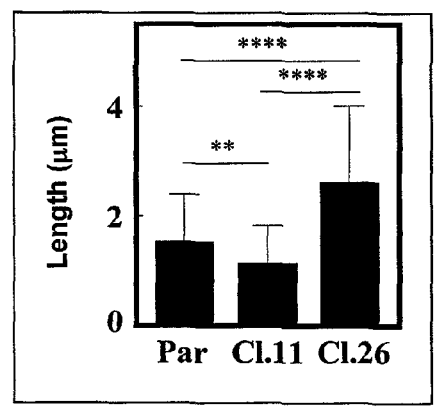

FIG. 10: illustrates the effect of the HER2 protein level on the length of mitochondria.

Figure 11:
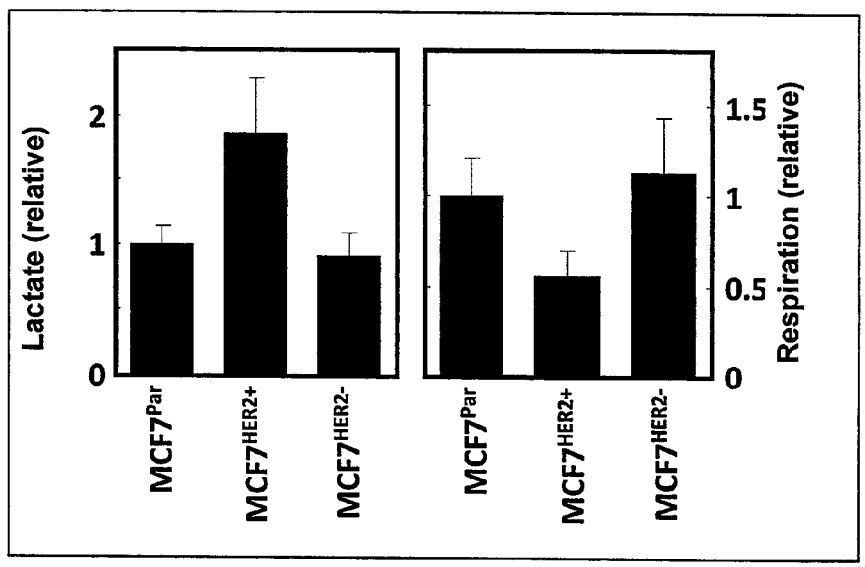

FIG. 11: shows the influence of the HER2 protein level on formation of lactate and mitochondrial respiration.

Figure 12:
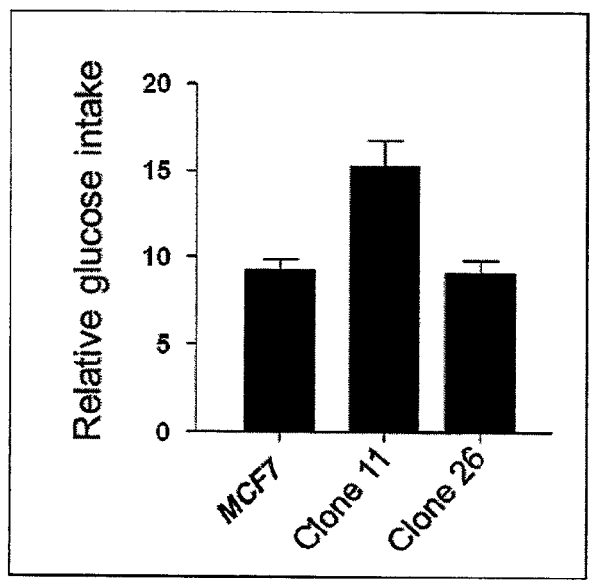

FIG. 12: shows that cells with high HER2 protein level feature increased uptake of glucose.

Figure 13:
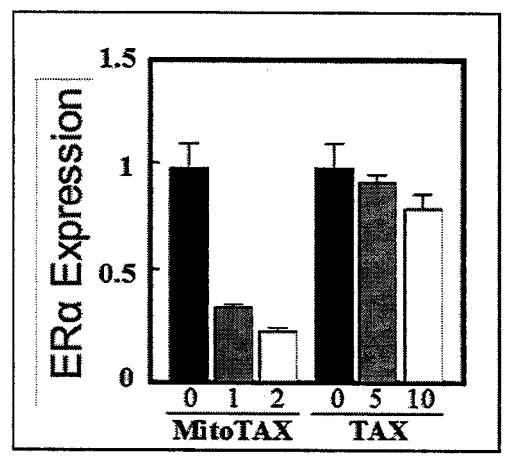

FIG. 13: shows that MitoTAX but not TAX reduces expression of the oestrogen receptor ERα.

Figure 14:
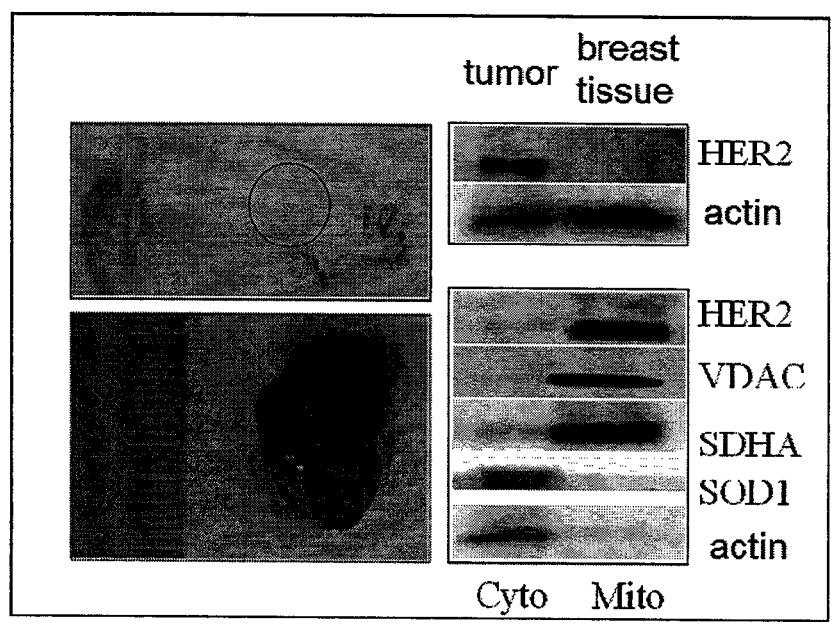

FIG. 14: shows that the HER2 protein is localised in mitochondria of cancer cells in spontaneous tumours with high HER2 level.

Figure 15:
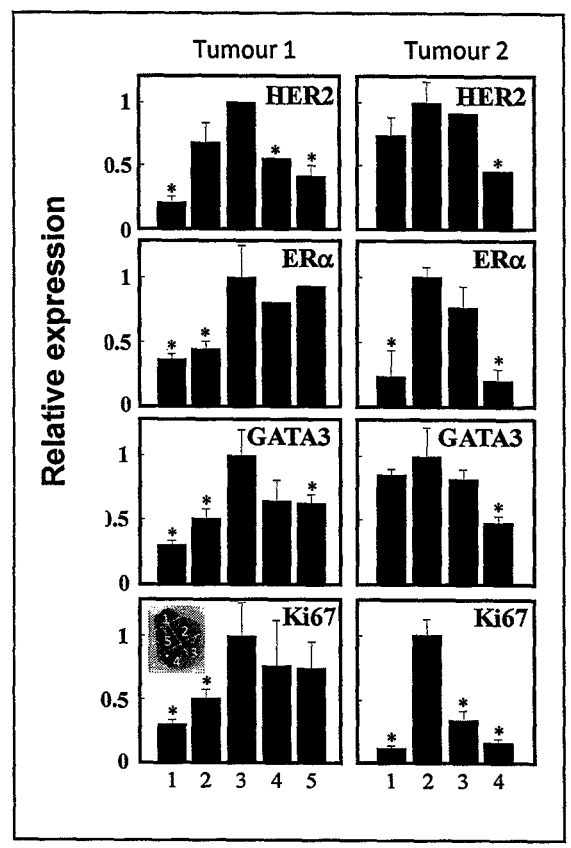

FIG. 15: shows that individual areas of mammary gland cancer in the FVB/N c-neu transgenic mouse differ in the expression of genes important for the development and treatment of breast cancer (HER2, ERα, GATA3, Ki67).

Figure 16:
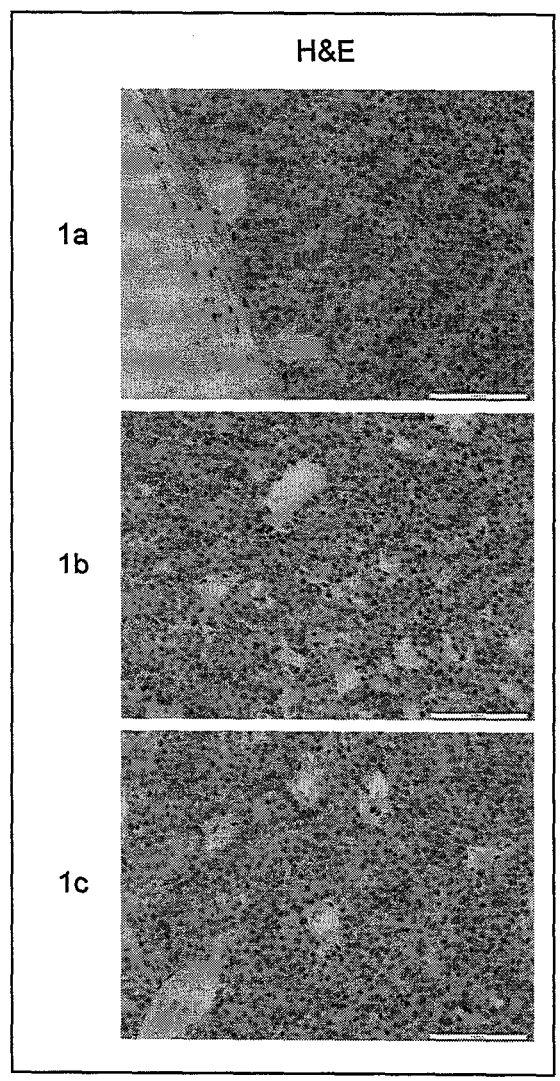

FIG. 16: illustrates sections of individual areas of the breast cancer stained by using the eosin-hematoxylin method to reveal the tumour morphology of the sections.

Figure 17:
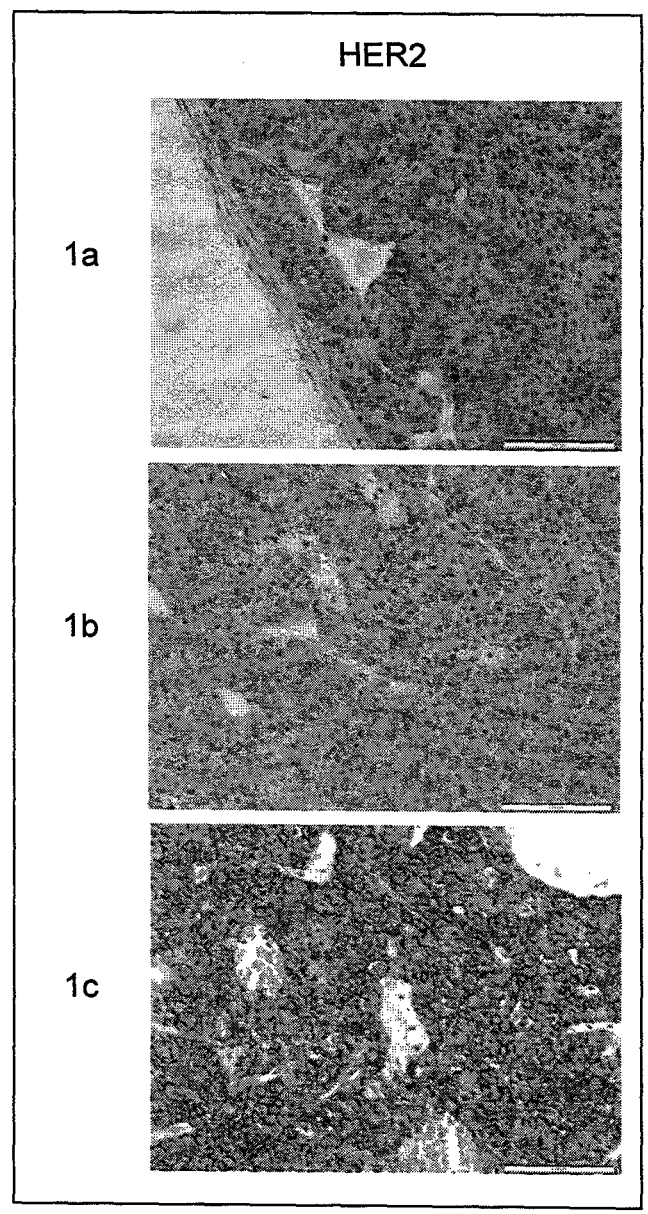

FIG. 17: shows sections of individual parts of the same tumours with a markedly diverse HER2 protein levels.

Figure 18:
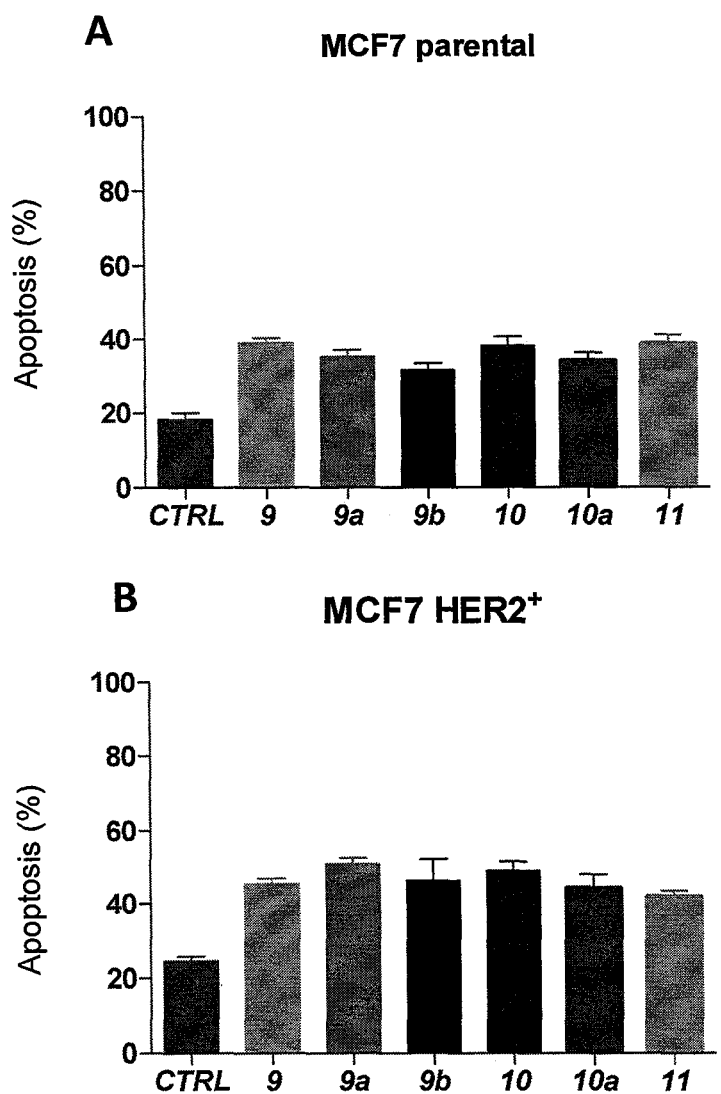
Figure 19:
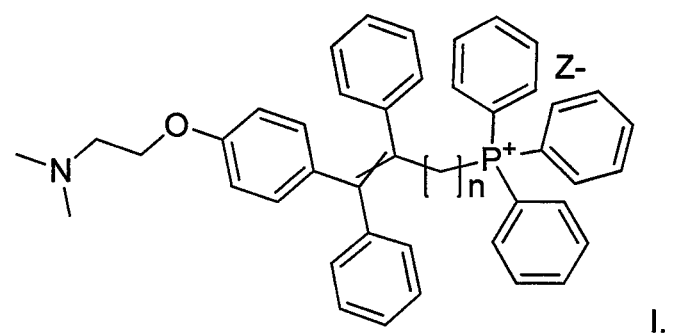
Figure 19:
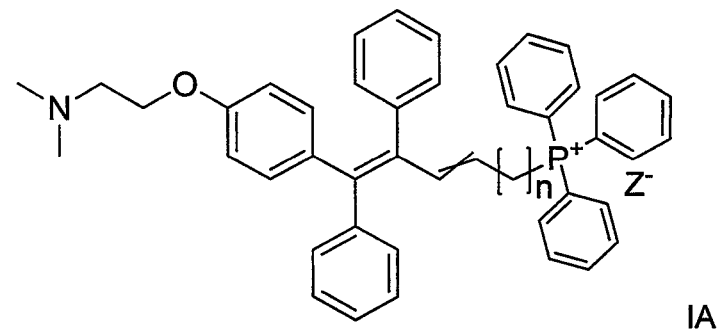

FIG. 18: illustrates level of apoptosis in MCF7 (A) and MCF7 HER2$^+$ cells (B) exposed to various MitoTAX derivatives

EXAMPLES

Aldehyde of the formula III, which was prepared according to the procedure published in 2003 ((Z)-Tamoxifen and Tetrasubstituted Alkenes and Dienes via a Regio- and Stereospecific Three-Component Magnesium Carbometalation Palladium(0) Cross-Coupling Strategy; Pierre E. Tessier, Andrea J. Penwell, Fabio E. S. Souza, and Alex G. Fallis*; ORGANIC LETTERS, 2003, Vol. 5, No. 17, 2989-2992.), was used as the starting material for preparation of alkyl triphenylphosphonium derivatives of tamoxifen of the general formula I and/or IA (MitoTAX),

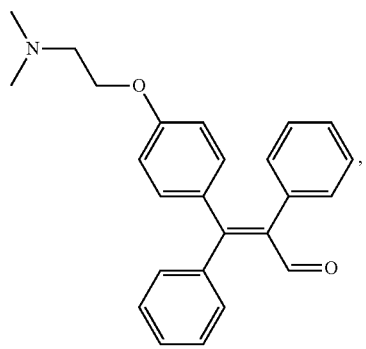

III

The starting aldehyde III, as the authors of the invention presented found out, can be prepared with the use of another oxidation agent than the one used in the above mentioned publication. They found out that application 2-iodobenzoic acid (IBX) instead of Dess-Martin agents forms only one double bond isomer. The yield is comparable.

IBX (12.460 g, 44.498 mmol) and the starting allyl alcohol (5.54 g, 14.833 mmol) (see the above mentioned publication) was dissolved in ethyl acetate (120 ml). The suspension was refluxed for the time of 3 hours under a constant stirring. The reaction mixture was cooled down to the room temperature, diluted with diethyl ether (1 l) and washed with saturated solution of sodium carbonate (3×100 ml). Combined aqueous layers were reextracted with ethyl acetate (3×80 ml) again. Combined ethyl acetate layers were dried over magnesium sulphate. The desiccant was filtered and the solution was concentrated under reduced pressure to yield 4.850 g (88%) of aldehyde III in the form of a brownish solid.

Example 1

(9-((tert-butyldimethylsilyl)oxy)nonyl)triphenylphosphonium bromide (634 mg, 1.057 mmol) was dissolved in dry tetrahydrofuran (THF) (6 ml), covered with argon atmosphere and cooled down to −78° C. Butyl lithium (1.2 ml, 0.9 M solution in THF) was slowly added dropwise to the reaction mixture under argon atmosphere. The solution was allowed to warm up to 0° C., colour was changed to dark red, cooled to −78° C. again and aldehyde of the formula III (160 mg, 0.430 mmol) dissolved in dry THF (3 ml) was added dropwise. Then the reaction mixture was allowed to warm up to the laboratory temperature and stirred for 16 hours under argon atmosphere. Progress of the reaction was monitored with thin layer chromatography (TLC) in the mixture of chloroform-methanol (10:1). Then saturated solution of ammonium chloride and water was added to the reaction mixture and extracted with ethyl acetate. The ethyl acetate layer was washed with brine and dried over magnesium sulphate. The solution was filtered and concentrated under reduced pressure. Chromatography of the concentrate on the column of silica gel in the system of dichloromethane (DCM)/methanol (gradient 0 to 10% of methanol) yielded 147 mg of product of the formula 4 (56% yield).

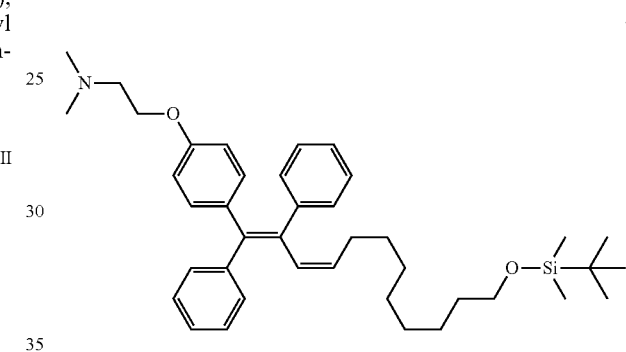

4

$^1$H NMR (500 MHz, cdcl3) δ 7.42-7.36 (m, 5H), 7.18-7.28 (m, 5H), 6.94 (d, J=8.7, 2H), 6.73 (d, J=8.7, 2H), 6.19 (d, J=11.5, 1H), 5.47 (dt, J=11.5, 7.4, 1H), 4.09 (t, J=5.8, 2H), 3.72 (t, J=6.6, 2H), 2.80 (t, J=5.8, 2H), 2.42 (s, 6H), 1.69-1.57 (m, 4H), 1.48-1.13 (m, 10H), 1.03 (s, 9H), 0.18 (s, 6H). Electrospray ionization mass spectrometry (ESI MS): 612.

(9-((tert-butyldimethylsilyl)oxy)nonyl)triphenylphosphonium bromide was prepared according to the procedure published in the literature. (Tetrahedron Letters, 2010, 51, 49, 6426-6428.)

Example 2

Silylated derivative of the formula 4 (147 mg, 2.240 mmol) was dissolved in THF (5 ml), then covered with argon atmosphere and tetrabutylammonium fluoride (TBAF) (260 μl, 1M solution in THF) was added dropwise at a temperature of 0° C. under the stirring. Then the reaction mixture was allowed to warm up to laboratory temperature and stirred for another 6 hours. Progress of the reaction was monitored with TLC in the mixture of chloroform-methanol (10:1). Then water was added and the mixture was extracted with ethyl acetate. The ethyl acetate layer was washed with saturated solution of soda and brine and dried over magnesium sulphate. The desiccant was filtered and the solution was concentrated under reduced pressure. The concentrate was purified with the column chromatography on silica gel in the system chloroform/methanol (gradient 0 to 10% of methanol) to yield 115 mg (96% yield) of the required alkenol of the formula 5.

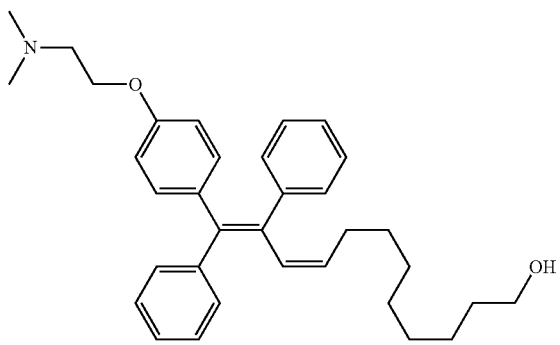

5

¹H NMR (500 MHz, cdcl3) δ 7.43-7.14 (m, 5H), 6.94 (d, J=8.5, 2H), 6.72 (d, J=8.5, 2H), 6.20 (d, J=11.5, 1H), 5.48 (dt, J=11.5, 7.4, 1H), 4.12 (t, J=5.9, 2H), 3.72 (t, J=6.6, 2H), 2.86 (t, J=5.9, 2H), 2.46 (s, 6H), 1.71-1.58 (m, 4H), 1.51-1.10 (m, 10H). ESI MS: 498.

Example 3

Alkenol derivative of the formula 5 (115 mg, 0.231 mmol) was dissolved in absolute ethanol (6 ml) and covered with argon atmosphere. 10% Pd/C (10 mg) was added to the mixture and the flask with reaction suspension was evacuated and covered with hydrogen atmosphere repeatedly for several times. Then the reaction mixture was stirred at the laboratory temperature under the hydrogen atmosphere for 24 hours. Progress of the reaction was monitored with TLC in the mixture of chloroform-methanol (10:1). The mixture was filtered through a layer of Celite and washed several times with ethanol. Ethanol was evaporated to yield 101 mg (87% yield) of the required alcohol of the formula 6, which is used without any further purification for the next step of the synthesis.

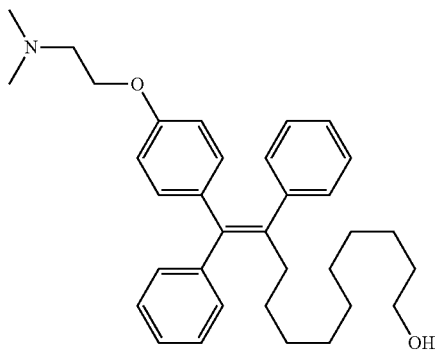

6

¹H NMR (500 MHz, cd3od) δ 7.40-7.01 (m, 10H), 6.85 (d, J=8.1, 2H), 6.68 (d, J=8.1, 2H), 4.20 (s, 2H), 3.55 (t, J=6.4, 2H), 3.46 (s, 2H), 2.89 (s, 6H), 2.42 (t, J=7.8, 2H), 1.57-1.48 (m, 2H), 1.38-1.11 (m, 12H). ESI MS: 500.

Example 4

Alcohol of the formula 6 (230 mg, 0,460 mmol) was dissolved in DCM (10 ml). CBr₄ (480 mg, 1.447 mmol) was added to the mixture at the laboratory temperature under argon atmosphere. Then triphenylphosphine (400 mg, 1.525 mmol) dissolved in DCM (3 ml) was added dropwise. The mixture was stirred at the laboratory temperature for 2 hours and then concentrated under reduced pressure. Progress of the reaction was monitored with TLC in the mixture of chloroform-methanol (10:1). Chromatography of the concentrate on the column of silica gel in the DCM/methanol system (gradient 0-10%) afforded 273 mg (92% yield) of required bromide of the formula 7. Bromide was subjected to the next reaction without any long storage.

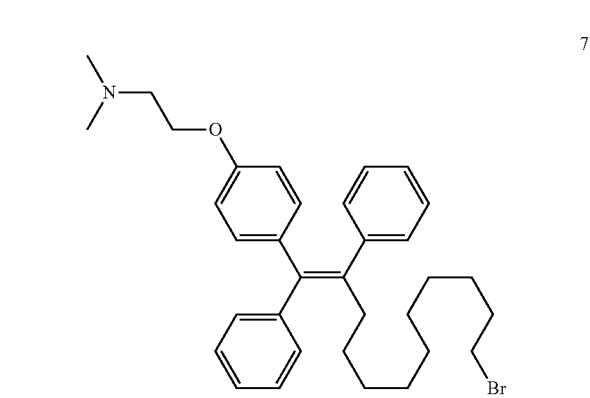 [SMILES: CN(C)CCOc1ccc(/C(=C(/CCCCCCCCCCBr)c2ccccc2)c2ccccc2)cc1]

7

¹H NMR (400 MHz, cdcl3) δ 7.46-6.96 (m, 10H), 6.78 (d, J=8.9 Hz, 2H), 6.53 (d, J=8.8 Hz, 2H), 4.29 (t, J=6.6 Hz 2H), 3.47-3.28 (m, 4H), 2.82 (s, 6H), 2.38 (t, J=7.8 Hz, 2H), 1.80 (q, J=7.8 Hz, 2H), 1.46-0.98 (m, 14H). ESI MS: 561.

Example 5

Alcohol of the formula 6 (102 mg, 0.204 mmol) was dissolved in DCM (6 ml). Triphenylphosphine (83 mg, 0.316 mmol) and imidazol (27 mg, 0.397 mmol) were added to the mixture at laboratory temperature, and the reaction mixture was cooled in an ice bath to 4° C. Iodine (76 mg, 0.302) was added to the cooled reaction mixture and stirred at the laboratory temperature for the time of 4 hours. Progress of the reaction was monitored with TLC in the mixture of chloroform-methanol (10:1). The reaction mixture was diluted with dichloromethane and extracted with thiosulphate. The organic phase was further washed with saturated solution of soda and brine and dried over magnesium sulphate. Chromatography of the concentrate on the column of silica gel in the DCM/methanol system (gradient 0 to 10%) afforded 100 mg (80% yield) of the required iodide of the formula 8. Iodide was subjected to the next reaction without any long storage.

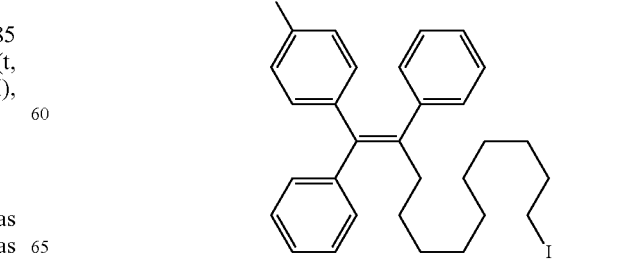

8

¹H NMR (400 MHz, cdcl3) δ 7.40-7.32 (m, 2H), 7.31-7.22 (m, 4H), 7.22-7.08 (m, 4H), 6.78 (d, J=8.8 Hz, 2H), 6.57 (d, J=8.8 Hz, 2H), 3.95 (t, J=5.8 Hz, 2H), 3.19 (t, J=7.0 Hz, 2H), 2.68 (t, J=5.8 Hz, 2H), 2.47-2.37 (m, 2H), 2.31 (s, 6H), 1.81 (q, J=7.0 Hz, 2H), 1.52-1.00 (m, 14H). ESI MS: 610.

Example 6

Triphenylphosphine (300 mg, 1.144 mmol) was added to bromide of the formula 7 (273 mg, 0.425 mmol), and the mixture was stirred at the temperature of 85° C. under argon atmosphere for the time of 12 hours. Progress of the reaction was monitored with TLC in the mixture of chloroform-methanol (10:1). The reaction mixture was cooled to the laboratory temperature, dissolved in the minimum quantity of DCM and added dropwise to the hexane solution (50 ml) under a constant stirring at the temperature of 0° C. The formed precipitate was filtered, dissolved in a minimum quantity of DCM again and added dropwise to the diethyl ether solution (50 ml), under a constant stirring at the temperature of 0° C. The precipitate was filtered and dried under vacuum to obtain 281 mg (73% yield) of the required compound of the formula 9 in the form of yellowish powder.

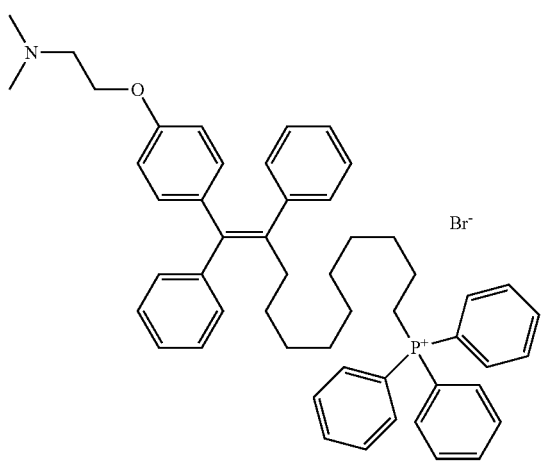

9

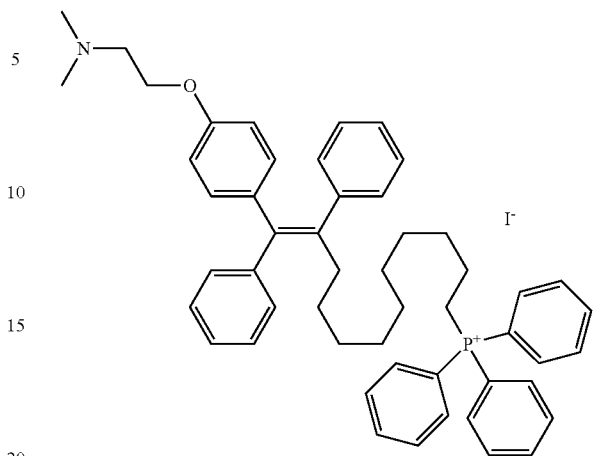

10

Example 21

The compound of the formula 5 can be obtained directly from aldehyde of the formula III by reaction with (9-hydroxynonyl)triphenylphosphonium bromide instead of (9-((tert-butyldimethylsilyl)oxy)nonyl)triphenylphosphonium bromide. Such synthesis is shorter and more cost-efficient. The main change is the use of the THF and DMSO mixture to increase solubility and the reaction can be carried out directly with (9-hydroxynonyl)triphenylphosphonium bromide, which was impossible in the actual THF. The procedure is carried out at room temperature instead of −78° C. This procedure leads also to a significant reduction of the total time of preparation of the compound required.

Preparation of the Compound of the Formula 5

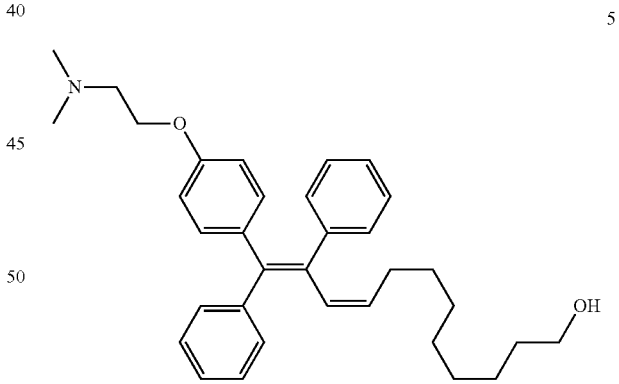

5

¹H NMR (500 MHz, cd3od) δ 7.89-7.74 (m, 15H), 7.37-7.05 (m, 10H), 6.85 (d, J=8.7, 2H), 6.71 (d, J=8.7, 2H), 4.24 (t, J=5.0, 2H), 3.57 (t, J=5.0, 2H), 3.43 (m, 2H), 2.97 (s, 6H), 2.40 (t, J=7.9, 2H), 1.74-1.60 (m, 2H), 1.59-1.49 (m, 2H), 1.36-1.05 (m, 12H). ESI MS: 744.

Example 7

Application of a procedure similar to that stated in example 6 enables to obtain the compound of the formula 10 from iodide of the formula 8.

(9-hydroxynonyl)triphenylphosphonium bromide (3.920 g, 8.082 mmol) was dissolved in DMSO (10 ml) and then THF (30 ml) was added. LiHMDS solution (14.800 ml, 1M in THF) was added dropwise into the reaction mixture for the time of 3 minutes. The colour of the reaction mixture changed to bright orange. Then solution of aldehyde of the formula III (1.000 g, 2.694 mmol) in THF (15 ml) was added dropwise to the reaction mixture, and the reaction was stirred for another ten minutes at laboratory temperature. Progress of the reaction was monitored with TLC in the mixture of chloroform-methanol (10:1). The reaction mixture was poured to the cold saturated solution of ammonium chloride (100 ml) and extracted with diethyl ether (5×100 ml). Combined organic layers were dried over magnesium sulphate. The desiccant was filtered and the product was concentrated under vacuum. Raw material was dissolved in diethyl ether (10 ml) and saturated ether solution of HCl (5 ml) was added dropwise. Precipitated product was filtered and extracted by the solution of NaOH (5 ml, 1M) and diethyl ether (25 ml). The organic layer was dried over magnesium sulphate. The desiccant was filtered and the product was concentrated under vacuum to yield 1,102 g (82%) of the product of the formula 5 in the form of slightly yellowish oil which was thus ready for further reactions.

Example 22

From the compound of the formula 6 it is possible to prepare the compound of the formula 9a (tertiary amine hydrochloride) without the necessity to isolate the compound 7. The preparation time is reduced and the yield is higher.

Preparation of the Compound of the Formula 9a

Saturated ether solution of HCl (6 ml) was added to the alcohol of the formula 6 (300 mg, 0.600 mmol) dissolved in diethyl ether (6 ml) The mixture was concentrated in vacuum and dissolved in DCM (6 ml). $CBr_4$ (298 mg, 0.901 mmol) was added to the reaction mixture and after its complete dissolution triphenylphosphine (252 mg, 960 mmol) was added. The reaction was quenched after 5 minutes with addition of methanol (1 ml) and saturated ether solution of HCl (3 ml). The solution was concentrated in vacuum and triphenylphosphine (2.000 g, 7.625 mmol) was added. The reaction mixture was mixed overnight at the temperature of 100° C. The mixture was cooled down to room temperature and then it was dissolved in DCM (10 ml). The mixture was then cooled to room temperature, dissolved in DCM (10 mL) and added dropwise to a cold and vigorously stirred diethyl ether (100 mL). The precipitate was filtered and dried in vacuum to yield 334 mg of (74%) product of the formula 9a in the form of white, slightly oily solid. The product may be re-purified through recurrent dissolution in DCM (2 ml) and subsequent precipitation in diethyl ether (20 ml).

Example 23

Preparation of the Compound of the Formula 11-Isomeric Alkenyl Triphenylphosphonium Derivative of Tamoxifen Nonan-1,9-diylbis(triphenylphosphonium)bromide was prepared from 1,9-dibromnonan and triphenylphosphine mixture stirred in the solution of dimethylformamide at the temperature of 100° C. for 16 hours and subsequent crystallisation from ethyl acetate.

Nonan-1,9-diylbis(triphenylphosphonium)bromide (545 mg, 674 mmol) was dissolved in DMSO (1 ml) and then THF (3 ml) was added. A solution of LiHMDS (670 µl, 1M in THF) was added dropwise into the reaction mixture for the time of 3 minutes. The colour of the reaction mixture changes to bright orange. Then a solution of aldehyde of the formula III (100 mg, 0.269 mmol) in THF (1 ml) was added to the reaction mixture dropwise and the reaction was stirred for another ten minutes at room temperature. Progress of the reaction was monitored with TLC in the mixture of chloroform-methanol (10:1). The reaction mixture was poured into a cold saturated solution of ammonium chloride (10 ml) and extracted with dichloromethane (5×20 ml). Combined organic layers were dried over magnesium sulphate. The desiccant was filtered and the product was concentrated in vacuum. Chromatography of the concentrate on the column of silica gel in the chloroform/methanol system (gradient 0-10%) yielded 56 mg (30%) of the required product of the formula 11.

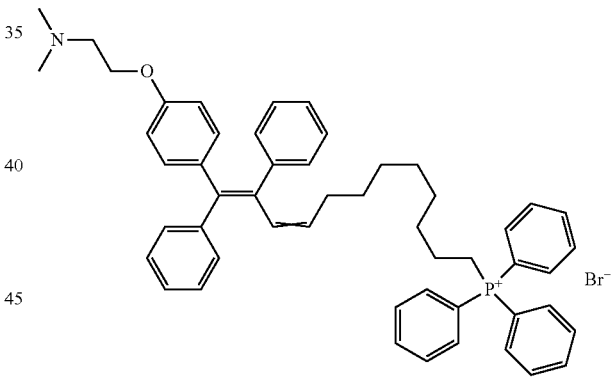

11

$^1$H NMR (400 MHz, cdcl3) δ 8.00-7.52 (m, 15H), 7.25-7.11 (m, 6H), 7.11-6.96 (m, 4H), 6.72 (d, J=8.3 Hz, 2H), 6.53 (d, J=8.3 Hz, 2H), 6.00 (d, J=11.5 Hz, 1H), 5.26 (dt, J=11.5, 7.4 Hz, 1H), 4.02 (t, J=4.8 Hz, 1H), 3.80-3.53 (m, 2H), 2.88 (t, J=5.3 Hz, 2H), 2.42 (s, 6H), 2.06-1.79 (m, 2H), 1.64-1.36 (m, 4H), 1.38-1.05 (m, 4H), 1.06-0.73 (m, 4H). ESI MS: 742.

Biological Tests of the Mitochondrially Targeted Alkyl Triphenylphosphonium Derivative of Tamoxifen (MitoTAX), Comparison Study with Tamoxifen (TAX)

The following examples 8-20 were carried out with the MitoTAX substance of the general formula I, where n=10.

Example 8

MitoTAX prepared according to Example 6 was tested for its effect on breast cancer cell lines. Lines with different levels of HER2 protein expression and oestrogen receptor α.

(ERα) were used. The cell line MCF7 features a relatively low expression of the HER2 protein. For the testing of killing of breast cancer cells with different HER2 protein levels by MitoTAX, we prepared HER2− and HER+ MCF7 cells. MCF7 cells were transfected with the vector with a 'non-silencing' sequence (NS), with a 'short hairpin' sequence attenuating the expression of HER2 (sh) and with the vector with a gene for HER2. FIG. 2 shows the expression of the HER2 protein in the various sublines using the western blotting method. In the subsequent work, the sublines NS, Sh1 26 (clone 26) and +11 (clone 11) were used.

Example 9

We evaluated the $IC_{50}$ values for TAX and MitoTAX for various breast cancer cell lines. The individual values were determined from the survival curves of cells at various concentrations of both substances using the crystal violet method. We used cellular lines with various levels of the HER2 and ERα protein ERα$^+$/HER2$^{low}$ (MCF7$_{par}$), ERα$^+$/HER2$^+$ (MCF7$_{HER2+}$, BT474, NeuTL—murine line of mammary gland cancer), ERα$^+$/HER2$^-$ (MCF7$_{HER2-}$, T47D, ZR75-1), ERα$^-$/HER2$^+$ (SK-BR-3), ERα$^-$/HER$^-$ (MDA-MB-231, MDA-MB-453, MDA-MB-436). From Table I, it is clear that the $IC_{50}$ value is significantly lower for MitoTAX, approximately by one order of magnitude. The most sensitive is the MCF7$_{HER2+}$ subline with the ERα$^+$/HER2$^+$ genotype. The corresponding lines with the ERα$^+$/HER2$^-$ (MCF7$_{HER2}$) and ERα$^+$/HER2$^{low}$ genotype (MCF7$_{par}$) feature $IC_{50}$ values which are approx. twice higher, which points o the fact that increased HER2 protein level leads to an increase in the sensitivity to MitoTAX. On the other hand and in contrary to MitoTAX, the sensitivity of HER2-high cells to TAX decreases. This indicates a unique property of MitoTAX that (to the best of our knowledge) has not been reported for any other anti-cancer substance.

TABLE I $IC_{50}$ values (μM) for breast cancer cellular lines with different expressions of the HER2 and ERα protein.

| Cellular line | Status | TAX | MitoTAX |
|---|---|---|---|
| MCF7$_{par}$ | ERα$^+$/HER2$^{low}$ | 15.2 | 1.25 |
| MCF7$_{HER2-}$ | ERα$^+$/HER2$^-$ | 14.1 | 1.45 |
| MCF7$_{HER2+}$ | ERα$^+$/HER2$^+$ | 21.6 | 0.65 |
| T47D | ERα$^+$/HER2$^-$ | 17.3 | 3.4 |
| MDA-MB-231 | ERα$^-$/HER$^-$ | 35.8 | 6.2 |
| MDA-MB-453 | ERα$^-$/HER$^-$ | 17.5 | 2.5 |
| MDA-MB-436 | ERα$^-$/HER$^-$ | 12.6 | 3.4 |
| ZR75-1 | ERα$^+$/HER2$^-$ | 16.9 | 2.7 |
| SK-BR-3 | ERα$^-$/HER2$^+$ | 28.3 | 3.5 |
| BT474 | ER$^+$/HER2$^+$ | 29.8 | 2.4 |
| NeuTL | ERα$^+$/HER2$^+$ | 35.6 | 4.5 |

Example 10

We also investigated whether MitoTAX suppresses growth of tumours. The anti-cancer efficacy of MitoTAX was tested using the transgenic mouse strain FVB/N c-neu that is born tumour-free and that in the adult age features increased HER2 protein expression due to the action of oestrogen (Guy C T et al. Expression of the neu protooncogene in the mammary epithelium of transgenic mice induces metastatic disease. Proc Natl Acad Sci USA 1992; 89:10578-10582.). These mice develop dysplasia and then hyperplasia in the region of mammary gland at 3 to 4 months after birth and form palpable tumours after 6 months. Importantly, this occurs in the context of the functional immune system. This model of breast cancer (mammary gland) is a very good approximation of the human breast cancer with a high HER2 protein level of the 'ductal in situ' type. Our results (FIG. 3) indicate a very good efficacy of MitoTAX on the growth of these tumours. Mice were administered a dose of 3 μmol of TAX and 0.5 μmol of MitoTAX twice a week for the time of two weeks. The volume of the tumours was quantified using ultrasound imaging that can visualise tumours with high precision and in a non-invasive way, including the embedded parts. It is clear that MitoTAX is approximately 20 to 30 times more efficient than TAX, and the differences between the action of both agents are highly significant. The symbol '*' indicates significant differences between treated and reference animals, the symbol '**' indicates significant differences between animals treated with TAX and those treated with MitoTAX. No apparent toxicity was observed in the experimental animals. The photographs below the chart show representative tumours from individual groups of animals.

Example 11

An important aspect of MitoTAX is its higher growth-suppressing activity towards the lines with increased expression of the HER2 oncogene. This is shown in FIG. 4, which also documents that the line with reduced expression of the HER2 oncogene (clone 26) is less responsive to MitoTAX, whilst it is exactly opposite for TAX. For these experiments we also prepared an MCF7 subline resistant to TAX by long-term exposure of the parental MCF7 cells to escalating doses of TAX. It is possible to see that these cells, resistant to TAX, were sensitive to MitoTAX (FIG. 4). The results in FIG. 4 illustrate the survival of breast cancer sublines derived from MCF7 cells with various genotypes (ERα$^+$/HER2$^{low}$, MCF7$_{par}$; ERα$^+$/HER2$^+$, MCF7$^{HER2+}$-clone 26; ERα$^+$/HER2$^-$, MCF7$^{HER2-}$-clone 11; ERα$^+$/HER2$^{low}$, MCF7$^{TAX-R}$). The results were obtained using the crystal violet method, which makes it possible to discriminate living and dead cells, in the presence of various concentrations of MitoTAX and TAX.

Example 12

An important characteristic of anti-cancer substances that cause death of cancer cells is the mode of cell death. For this reason we tested whether MitoTAX causes apoptosis, i.e. programmed cell death when a cell is dies in a controlled way and its residual apoptotic bodies are removed from the tissue by phagocytic cells without inflammatory reactions. FIG. 5 shows that the agent, indeed, caused apoptosis. Apoptosis was evaluated on the basis of assessing of percentage of cells with annexin V in the external part of the plasma membrane by means of flow cytometry. Once again, the results document increased efficacy of MitoTAX to cells with high HER2 protein, while cells with a reduced HER2 protein level are more resistant (albeit still undergoing apoptosis).

Example 13

Previous publication (Moreira P I et al. Tamoxifen and estradiol interact with the flavin mononucleotide site of complex I leading to mitochondrial failure. J Biol Chem 2006; 281:10143-10152.) indicated that the target for TAX in mitochondria is, at a high level of the agent, complex I.

We have found out that this holds also for MitoTAX, which is documented in FIG. 6. This documents also in inhibitory effect of TAX (on the left) and MitoTAX (on the right) on respiration via the mitochondrial complexes I and II. It is possible to see that TAX inhibits preferably complex I to complex II, at concentrations exceeding 20 μM. MitoTAX also inhibits complex I preferably to complex II, but at significantly lower concentrations of about 1 to 2 μM. For these assays, MCF7 cells were placed in the chamber of the Oxygraf instrument and the respiration was determined at increasing doses of TAX (on the left) and MitoTAX (on the right). Respiration (oxygen consumption linked with ATP formation) is related to $10^6$ cells and is shown as a relative value with the beginning level of respiration marked with the relative value of 1.

Example 14

A property typically associated a number of mitocans is their ability to increase oxidative stress (formation of reactive oxygen species, ROS), selectively in cancer cells, especially associated with their action on mitochondrial complexes participating with oxidative phosphorylation. This is usually connected with a decrease in the mitochondrial potential (Neuzil J et al. Classification of mitocans, anti-cancer drugs acting on mitochondria. Mitochondrion 2013; 13:199-208. Kluckova K et al. Mitochondrial complex II, a novel intriguing target for anti-cancer agents. Biochim Biophys Acta 2013; 1827:552-564.). We tested formation of ROS also for MitoTAX. FIG. 7 shows generation of ROS for MCF7 sublines of differing in HER2 levels, after 1 h exposure to TAX or MitoTAX (both at 5 μM). It is possible to see that TAX is markedly less effective at the same concentration than MitoTAX. Another important finding is that MitoTAX induces formation of more ROS in cells with high HER2 levels, whilst a lower production of ROS occurs in cells with low HER2. TAX does not follow this trend. In all cases, the uncoupler of mitochondrial respiration (CCCP), reduces the mitochondrial potential to its basal value. FIG. 8 shows that MitoTAX (but not TAX) reduces the mitochondrial potential already at the concentration of 5 μM and within 1 h.

Example 15

In breast cancer cells with high level of the HER2 protein, the protein is localised preferably in mitochondria. This is shown in FIG. 9, where the western blot of the original line MCF7 as well as sublines HER2+ MCF7 (clone 11), HER2− MCF7 (clone 26) is represented, and where it is seen that the actual sublines are resistant to TAX (clone TAM-R). It is possible to see that clone 11 cells feature increased expression of the HER2 protein (marked with an arrow) in the mitochondrial, cytoplasmic (it contains plasmatic membrane) as well as nuclear fractions. The lower figure shows the mitochondrial fraction when the membrane was exposed for a longer period of time, so that it can be clear that in mitochondria, albeit at a significantly lower level, the HER2 protein is present also in parental MCF7 cells and in cells resistant to TAX, but not in cells with reduced HER2 (clone 26). This surprising result is in agreement with the recently published work (Ding Y et al. Receptor tyrosine kinase ErbB2 translocates into mitochondria and regulates cellular metabolism. Nat Commun 2012; 3:1271). This publication also shows that breast cancer cells with high expression of the HER2 protein localised predominantly in mitochondria, are resistant to trastuzumab. During application of trastuzumab to cancer cells, more HER2 protein was mobilised to mitochondria (Ding Y et al. Receptor tyrosine kinase ErbB2 translocates into mitochondria and regulates cellular metabolism. Nat Commun 2012; 3:1271.). It is possible that breast cancer cells mobilise the HER2 protein away from their surface (plasma membrane), so that the protein cannot be affected by trastuzumab. One of the HER2 inhibition results is the activation of the p27 protein, which is an inhibitor of the cell cycle, reducing the malignant nature of the cells (Yang H Y, Shao R, Hung M C, Lee M H. p27 Kip1 inhibits HER2/neu-mediated cell growth and tumorigenesis. Oncogene 2001; 20:3695-3702.). This has a negative impact on cancer cells with high level of the HER2 protein, because cancer cells are evolutionally programmed to maintain high proliferative status (Hanahan D, Weinberg R A. The hallmarks of cancer. Cell 2000; 100:57-70). Therefore we can speculate that, since the HER2 protein, the target of trastuzumab, is not present in the membrane at a major scale, the cell will acquire resistance to trastuzumab. Nevertheless, during this process it will increase its sensitivity to MitoTAX, which is able to penetrate into mitochondria, which further highlights its exceptional nature.

Example 16

One of the reasons for an increased sensitivity of breast cancer cells with high HER2 protein is their changed mitochondrial bioenergetics and morphology. The high level of the HER2 protein in mitochondria changes their morphology as well as function. FIG. 10 shows that mitochondria in the HER2+ cells (clone 11) are approximately twice shorter than those in the HER2− cells (clone 26). The mitochondrial length was estimated with the help of confocal microscopy of cellular lines transfected by the mitochondrially targeted GFP protein (which visualises mitochondria by means of green fluorescence). The length was determined by the analysis of mitochondria in 50 cells selected in a random manner using the Fuji Freehand Lines Measurement Tools software. This is linked to the reduced mitochondrial respiration and is associated with lower mitochondrial potential and higher production of lactate (a symptom of a shift towards aerobic glycolytic metabolism) (FIG. 11). It is shown that in this case, cells with increased HER2 protein levels produce approximately twice more lactate than parental cells and cells with reduced HER2 protein levels. In the case of respiration, it is exactly opposite. Cells with increased HER2 protein levels respire less (ATP production is associated with lower consumption of oxygen). A higher share of glycolysis in the ATP generation for cells featuring increased HER2 protein level is associated also with their increased uptake of glucose (FIG. 12).

Example 17

Another possible reason for increased sensitivity of HER2+ cells with high HER2 protein levels to MitoTAX is the effect of this agent on the oestrogen receptor ERα, having anti-apoptotic effects (Thomas C, Gustaffson J. The different roles of ER subtypes in cancer biology and therapy. Nat Rev Cancer 2011; 11:597-608. Deblois D, Giguere V. Oestrogen-related receptors in breast cancer: control of cellular metabolism and beyond. Nat Rev Cancer 2013; 13:27-36.). This is shown in FIG. 13, where it is possible to see that MitoTAX reduces the ERα expression already at a concentration of 1 μM approximately three times, while TAX is ineffective. These results were obtained using the real-time PCR methodology.

Example 18

The above mentioned high efficacy of MitoTA against tumours with high expression of the HER2 protein in the murine strain FVB/N c-neu is of high importance. This tumour, which corresponds to human tumours with high expression of the HER2 protein, was analysed for the expression of the HER2 protein and several other genes. FIG. 14 shows a representative FVB/N c-neu mouse with a tumour (the upper figure on the left) and also the excised tumour (the figure in the lower left corner). The results of the tumour analysis by western blotting documents that the tumour contains a high level of the HER2 protein, which is almost undetectable in the normal tissue of the mammary gland. The figure also shows results of the analysis of the mitochondrial (Mito) and cytosolic (Cyto) fractions. Antibodies against specific proteins are used as markers for the mitochondrial fraction. It is clear that an absolute majority of the HER2 protein is localised in mitochondria. These results obtained from an experimental tumour correspond to results from breast cancer cells with high expression of HER2.

Example 19

It has been shown recently in kidney tumours that the same tumour contains areas that differs in their mutation profile (Gerlinger M et al. Intratumor heterogeneity and branched evolution revealed by multiregion sequencing. N Engl J Med 2012; 366:883-892.). Tumour heterogeneity (Stingl J, Caldas C. Molecular heterogeneity of breast carcinomas and the cancer stem cell hypothesis. Nat Rev Cancer 2007; 7:791-799.), and this phenomenon was identified in the case of breast carcinomas as well. This is correlated, interestingly, with the finding that spontaneous tumours of the mammary gland in the FVB/N c-neu transgenic mouse contain areas with different expression of several important genes at the level of mRNA, which may considerably affect breast cancer treatment. This concerns the genes ERα, HER2, Ki67, a marker proliferation which is higher in case of higher levels of HER2) and GATA3 (transcription activator which positively affects HER2 expression). This is shown in FIG. 15. In this experiment, two tumours were divided into several parts, which were analysed using real-time PCR for the expression of the above mentioned genes. The results illustrate very different expression of the genes in the individual areas of the tumour, varying up to 5 times. Another proof of the different expression of the HER2 gene in individual parts of the tumour in the experimental FVB/N c-neu mice is shown in the following Figures, where it is possible to see the tumour morphology on the basis of staining with haematoxylin and eosin (FIG. 16), as well as an immunohistochemical analysis of the HER2 protein expression (FIG. 17). These unambiguous differences correspond to a different expression of HER2 in individual parts of the tumour at the level of mRNA and are consistent with published data on intratumour heterogeneity (Gerlinger M et al. Intratumor heterogeneity and branched evolution revealed by multiregion sequencing. N Engl J Med 2012; 366:883-892. Stingl J, Caldas C. Molecular heterogeneity of breast carcinomas and the cancer stem cell hypothesis. Nat Rev Cancer 2007; 7:791-799.). FIG. 17 shows that there are very large differences in the HER2 protein expression between the external part of the tumour (part 1a), middle part (part 1 b) and internal part (part 1c). This means that some tumour areas will be resistant to TAX therapy (areas with high HER2 protein expression), others will be resistant to the trastuzumab therapy (areas with low HER2 protein levels). Moreover, it is possible to expect that the trastuzumab action will be accompanied by an increased transfer of the HER2 protein to mitochondria, whereby the tumour areas with high HER2 protein expression acquire resistance to this type of therapy. On the other hand, MitoTAX, which acts on mitochondria and kills cells featuring high HER2 protein expression more efficiently than cells with low expression of this protein, is able to cope with the areas of tumours resistant to trastuzumab.

Example 20

MitoTAX, efficiently killing the breast cancer cells, is effective also against other types of cancer cells. This is shown in Table 2, where it is possible to see $IC_{50}$ values for MitoTAX and TAX for killing various types of cancer, including carcinomas, sarcomas and leukaemias. The $IC_{50}$ values were lower for MitoTAX than for TAX in all cases.

TABLE 2

| Cellular line - tumour type | TAX | MitoTAX |
| --- | --- | --- |
| 1321n1 - astrocytoma | 17.97 | 1.54 |
| SHSY5Y - neuroblastoma | 11.16 | 1.76 |
| U87 - glioblastoma | 32.44 | 1.96 |
| H28 - mesothelioma | 39.74 | 2.53 |
| LnCAP - prostate cancer | 36.70 | 0.86 |
| H1299 - non-small cell lung cancer | 38.53 | 1.80 |
| Hela - cervical cancer | 30.28 | 2.68 |
| MG-63 - osteosarcoma | 19.94 | 1.47 |
| HCT116 - colorectal cancer | 28.91 | 1.81 |
| HepG2 - hepatocarcinoma | 17.56 | 1.05 |
| MOLT-4 - leukaemia | 12.9 | 0.37 |

Example 24

FIG. 18 shows apoptosis induction by the effect of alkyl and alkenyl triphenylphosphonium derivatives of MitoTAX, as documented in Table 3, in breast cancer cells MCF7 (A) and the MCF7 cell subline with increased HER2 protein level (B). The percentage of apoptotic cells was determined using the specific apoptosis essay based on evaluation of the level of externalised annexin V by using flow cytometry. MCF7 and MCF7 HER2$^+$ cells were exposed to individual MitoTAX derivatives at the concentration of 2 μM for 24 h. The "CTRL" column indicates the percentage of apoptotic cells in the cell population without addition of the tested substances, and thus it corresponds to the basal level of apoptosis. All tested derivatives of MitoTAX induced apoptosis.

TABLE 3
| The compound of the formula 9 | | 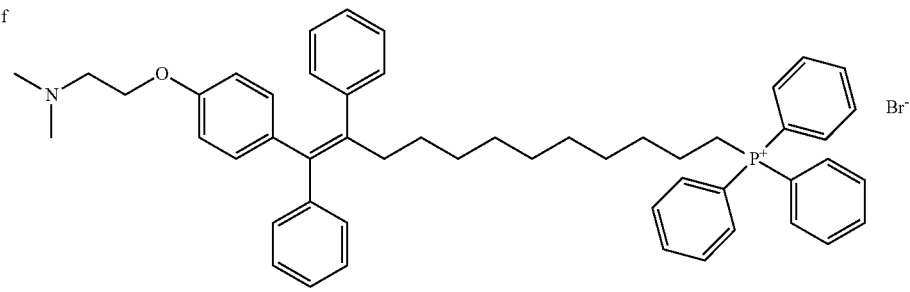 |
| --- | --- | --- |
| The compound of the formula 9a | HBr | 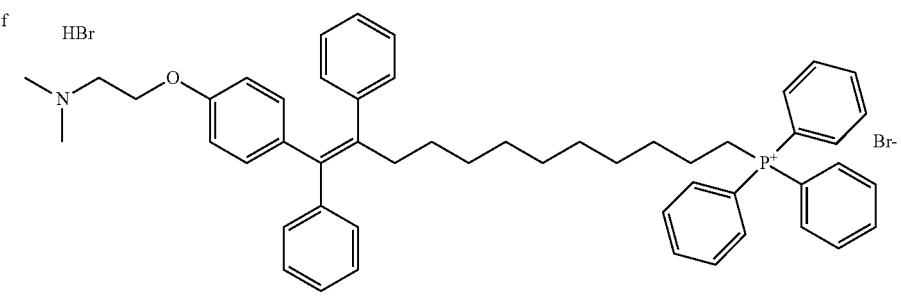 |
| The compound of the formula 9b | HCl | 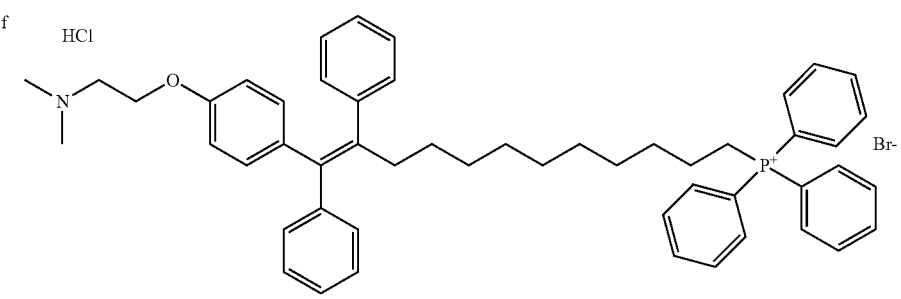 |
| The compound of the formula 10 | | 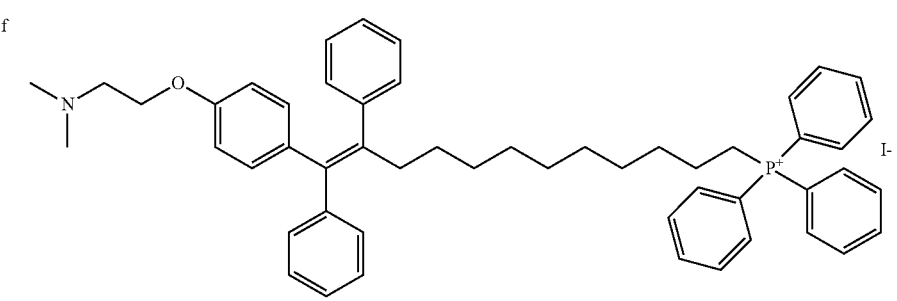 |
| The compound of the formula 10a | HI | 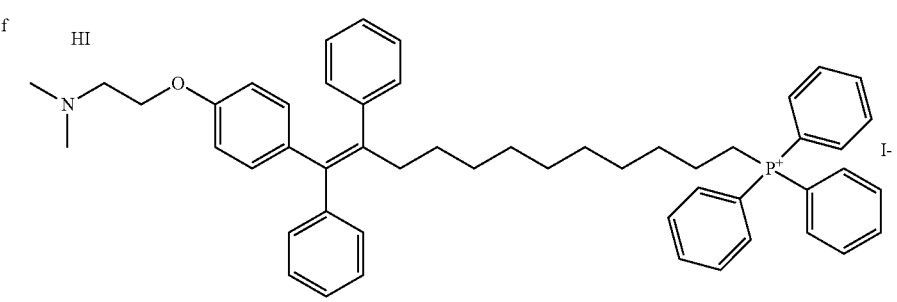 |

TABLE 3-continued

The compound of the formula 11

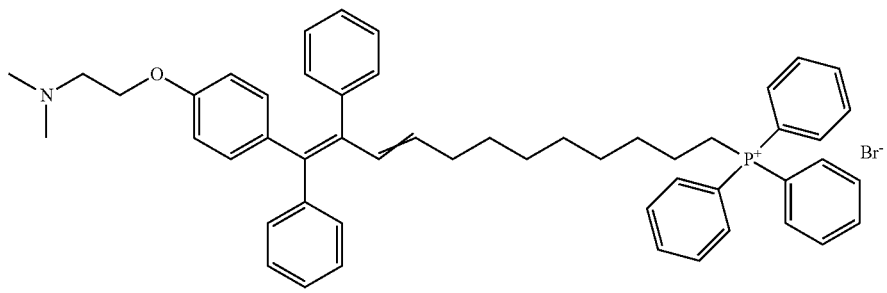 [SMILES: CN(C)CCOc1ccc(/C(=C(/C=CCCCCCCCC[P+](c2ccccc2)(c2ccccc2)c2ccccc2)c2ccccc2)c2ccccc2)cc1 ; [Br-]]

In conclusion it is possible to sum up that we have prepared brand new compounds which are based on TAX, which is a frequently used drug for the treatment of breast cancer, i.e. a disease with a rising incidence (DeSantis C et al. Breast cancer statistics, 2011. CA Cancer J Clin 2011; 1:409-4018.). The above described alkyl and alkenyl triphenylphosphonium derivatives of tamoxifen (MitoTAX) according to the invention are preferably accumulated in mitochondria, where their target site, the mitochondrial complex I, is located. The MitoTAX interaction with complex I will result in an interruption of the flow of electrons that then interact with molecular oxygen. This leads to the enhanced formation of ROS that, in turn, trigger cellular death.

MitoTAX is efficient to breast cancer with both low and high levels of the HER2 protein that considerably complicates the existing methods of treatment. Thus, MitoTAX can supplement or replace both TAX and trastuzumab in cancer therapies.

USE OF THE INVENTION

The new tamoxifen derivatives, of the general formulas I and IA according to the invention, are applicable for the treatment of cancer in the clinical setting and in the pharmaceutical industry for the preparation of drugs for efficient treatment of cancer.

The invention claimed is:
1. A mitochondrially targeted E/Z isomer of an aliphatic triphenylphosphonium derivative of tamoxifen of general formula I or IA,

I

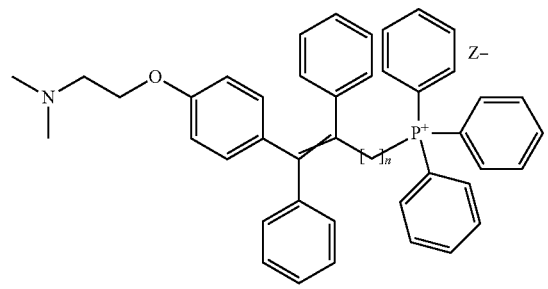

wherein n=8 to 12,
wherein Z is selected from the group consisting of anions of organic salts, anions of inorganic salts, and mixtures thereof, and
wherein the crossed double bond in general formula I indicates that the double bond may have E and/or Z configuration,

IA

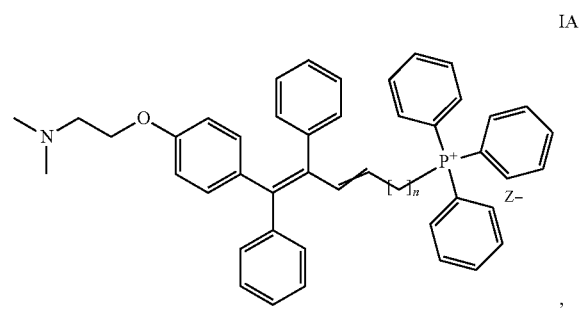

wherein n=6 to 10,
wherein Z is as defined above, and
wherein the crossed double bond in general formula IA indicates that the double bond may have E and/or Z configuration.

2. The mitochondrially targeted E/Z isomer of the aliphatic triphenylphosphonium derivative of tamoxifen of general formula I or IA according to claim 1, wherein Z is selected from the group consisting of citrate, acetate, lactate, tartrate, oxalate, ascorbate, mesylate, tosylate, sulphate, halogenide, phosphate, and mixtures thereof.

3. A method of preparing the mitochondrially targeted E/Z isomer of an alkyl triphenylphosphonium derivative of tamoxifen of general formula I according to claim 1, the method comprising the steps of:
generating, under the treatment of an organic base in tetrahydrofuran under an argon atmosphere at a temperature of −78° C., an ylide from tert-butyldimethylsilyl-oxy-alkyl-triphenylphosphonium of general formula II:

II

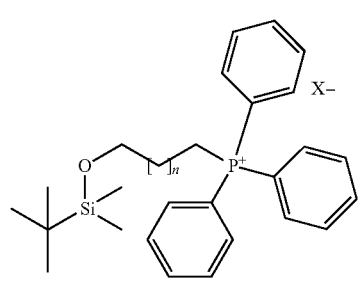

wherein n=5 to 9, and
wherein X is I, Br, Cl or mesyl,
condensing the ylide with an aldehyde of general formula III to form a silylated derivative of general formula IV:

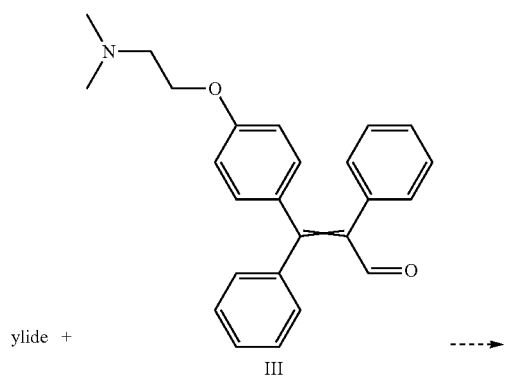

ylide +    III  ---→ treating the silylated derivative of general formula IV with tetrabutylammonium fluoride to form an alkenol of general formula V:

V reducing the alkenol of general formula V in a hydrogen atmosphere in the presence of a catalyst to form an alcohol of general formula VI,

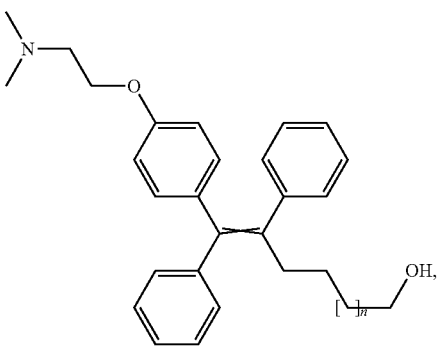

VI substituting the alcohol of general formula VI to form a derivative of general formula VII,

VII and
converting the derivative of general formula VII to the mitochondrially targeted E/Z isomer of an alkyl triphenylphosphonium derivative of tamoxifen of general formula I by heating with triphenylphosphine.

4. A method of preparing the mitochondrially targeted E/Z isomer of an alkyl triphenylphosphonium derivative of tamoxifen of general formula I according to claim 1, the method comprising the steps of:
condensing a (hydroxyalkyl)triphenylphosphonium bromide with an aldehyde of general formula III under the treatment of a base in a mixture tetrahydrofuran and dimethylsulphoxide at room temperature to form an alkenol of general formula V:

(hydyalkyl)triphenylphosphonium bromide +

III  ---→

-continued

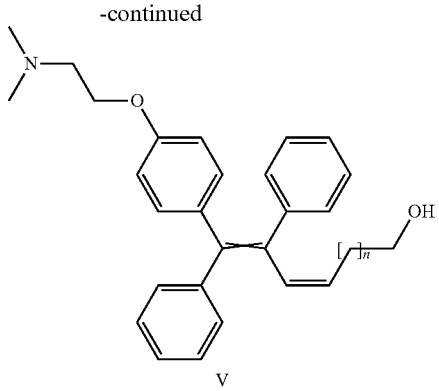

V wherein n=5 to 9, and
wherein X is I, Br, Cl or mesyl,
reducing the alkenol of general formula V in a hydrogen atmosphere in the presence of a catalyst to form an alcohol of general formula VI,

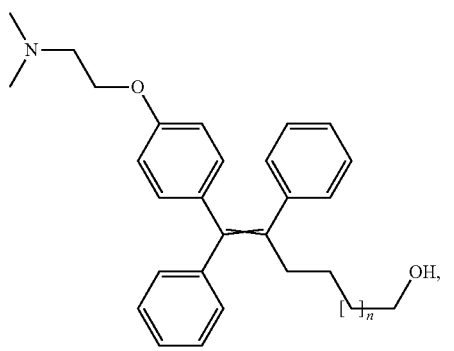

VI substituting the alcohol of general formula VI to form a derivative of general formula VII,

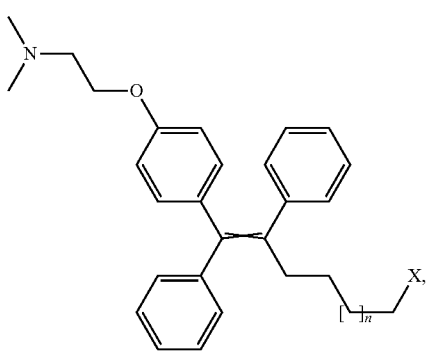

VII and
converting the derivative of general formula VII to the mitochondrially targeted E/Z isomer of an alkyl triphenylphosphonium derivative of tamoxifen of general formula I by heating with triphenylphosphine.

5. A method of preparing the mitochondrially targeted E/Z isomer of an alkylenyl triphenylphosphonium derivative of tamoxifen of general formula IA according to claim 1, the method comprising the steps of:

generating, in a mixture of tetrahydrofuran and dimethylsulphoxide in an argon atmosphere at room temperature under the treatment of organic base, an ylide from alkyl bis(triphenylphosphonium) with the general Formula XII:

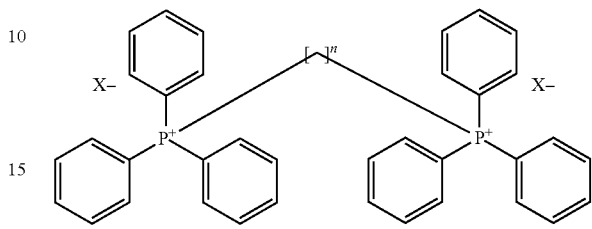

XII wherein n=7 to 11, and
wherein X is I, Br, Cl or mesyl or their combination, and subsequently condensing the ylide with an aldehyde of formula III to form the mitochondrially targeted E/Z isomer of an alkylenyl triphenylphosphonium derivative of tamoxifen of general formula IA:

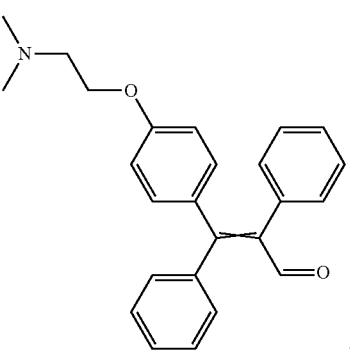

III

6. A method of treating neoplastic disease comprising administering the mitochondrially targeted E/Z isomer of an aliphatic triphenylphosphonium derivative of tamoxifen of general formula I or IA according to claim 1, wherein the neoplastic disease is selected from the group consisting of carcinoma, sarcoma, lymphoma and leukemia.

7. A method of treating neoplastic disease comprising administering the mitochondrially targeted E/Z isomer of an aliphatic triphenylphosphonium derivative of tamoxifen of general formula I or IA according to claim 1, wherein the neoplastic disease is selected from the group consisting of astrocytoma, neuroblastoma, glioblastoma, mesothelioma, breast cancer, prostate cancer, non-small cell lung cancer, cervical cancer, osteosarcoma, colorectal cancer, hepatocarcinoma, and leukemia.

8. A method of killing cancer cells in various regions of breast tumors, regardless of expression levels of HER2, ERα, GATA3 and Ki67 proteins comprising administering the mitochondrially targeted E/Z isomer of an aliphatic triphenylphosphonium derivative of tamoxifen of general formula I or IA according to claim 1.

9. A method of inhibiting respiration via the mitochondrial complex I comprising administering the mitochondrially targeted E/Z isomer of an aliphatic triphenylphosphonium derivative of tamoxifen of general formula I or IA according to claim 1.

10. A drug for the treatment of neoplastic disease, the drug comprising at least one mitochondrially targeted E/Z isomer of an aliphatic triphenylphosphonium derivative of tamoxifen of general formula I or IA according to claim 1.

11. The drug according to claim 10, wherein the neoplastic disease is breast cancer with a high HER2 protein level.

12. The drug according to claim 10, wherein the neoplastic disease is breast cancer with a low HER2 protein level.

13. The drug according to claim 10, wherein the drug is efficient against neoplastic disease with either low or high HER2 protein levels.

* * * * *